United States Patent
Hu et al.

(10) Patent No.: US 11,739,161 B2
(45) Date of Patent: Aug. 29, 2023

(54) METHODS FOR TREATING AND DIAGNOSING PROSTATE CANCER

(71) Applicant: Tufts Medical Center, Inc., Boston, MA (US)

(72) Inventors: Guo-fu Hu, Wellesley, MA (US); Shuping Li, Wellesley, MA (US)

(73) Assignee: Tufts Medical Center, Inc., Boston, MA (US)

( * ) Notice: Subject to any disclaimer, the term of this patent is extended or adjusted under 35 U.S.C. 154(b) by 91 days.

(21) Appl. No.: 16/647,294

(22) PCT Filed: Sep. 13, 2018

(86) PCT No.: PCT/US2018/050874
§ 371 (c)(1),
(2) Date: Mar. 13, 2020

(87) PCT Pub. No.: WO2019/055648
PCT Pub. Date: Mar. 21, 2019

(65) Prior Publication Data
US 2021/0122833 A1   Apr. 29, 2021

Related U.S. Application Data

(60) Provisional application No. 62/558,719, filed on Sep. 14, 2017.

(51) Int. Cl.
| | | |
|---|---|---|
| *C07K 16/40* | (2006.01) | |
| *A61P 35/00* | (2006.01) | |
| *A61K 31/436* | (2006.01) | |
| *A61K 31/4375* | (2006.01) | |
| *A61K 31/502* | (2006.01) | |
| *A61K 31/5377* | (2006.01) | |
| *C12N 15/113* | (2010.01) | |
| *C12Q 1/6886* | (2018.01) | |
| *G01N 33/574* | (2006.01) | |

(52) U.S. Cl.
CPC ............ *C07K 16/40* (2013.01); *A61K 31/436* (2013.01); *A61K 31/4375* (2013.01); *A61K 31/502* (2013.01); *A61K 31/5377* (2013.01); *A61P 35/00* (2018.01); *C12N 15/1137* (2013.01); *C12Q 1/6886* (2013.01); *G01N 33/57434* (2013.01); *G01N 33/57488* (2013.01); *C07K 2317/622* (2013.01); *C07K 2317/76* (2013.01); *C12Q 2600/106* (2013.01); *C12Q 2600/112* (2013.01); *C12Q 2600/118* (2013.01); *C12Q 2600/158* (2013.01); *G01N 2333/922* (2013.01)

(58) Field of Classification Search
CPC .................................................... C07K 16/40

USPC ....................................................... 424/135.1
See application file for complete search history.

(56) References Cited

U.S. PATENT DOCUMENTS

| | | | |
|---|---|---|---|
| 2002/0055627 A1 | 5/2002 | Rosen et al. | |
| 2003/0040617 A9 | 2/2003 | Rosen et al. | |
| 2006/0153808 A1* | 7/2006 | Cristofanilli ... | A61K 39/001151 424/93.2 |
| 2006/0183141 A1 | 8/2006 | Chang et al. | |
| 2007/0048738 A1 | 3/2007 | Donkena et al. | |
| 2010/0256232 A1* | 10/2010 | White ..................... | G01N 33/74 514/548 |
| 2013/0331281 A1 | 12/2013 | Tsai et al. | |
| 2015/0218655 A1 | 8/2015 | Mercola et al. | |
| 2016/0361380 A1* | 12/2016 | Averback ............. | A61K 31/517 |
| 2017/0183744 A1* | 6/2017 | Paris ..................... | G16B 30/00 |

FOREIGN PATENT DOCUMENTS

| | | |
|---|---|---|
| WO | WO-2010/065940 A1 | 6/2010 |
| WO | WO-2013/025322 A2 | 2/2013 |

OTHER PUBLICATIONS

Penney et al (Journal of Clinical Oncology, 2011, 29(17): 2391-2396).*
Gamper et al (BMC Genomics, 2009, 10(199): 1-17).*
Timms et al (Proteomics Clin. 2014, 8: 982-993).*
Seol et al (Exp Oncol, 2005, 27(2): 120-124).*
Floc'h et al (Cancer Research, 2012, 72(17): 4483-4493).*
International Search Report and Written Opinion for PCT International Application No. PCT/US2018/050874, dated Jan. 18, 2019 (19 pages).
Li et al., "Ribonuclease 4 protects neuron degeneration by promoting angiogenesis, neurogenesis, and neuronal survival under stress," Angiogenesis 16(2):387-404 (2012).
International Preliminary Report on Patentability for PCT International Application No. PCT/US2018/050874, dated Mar. 26, 2020 (12 pages).
Office Action dated Jan. 5, 2023, for Chinese Patent Application No. 201880073570.X, Hu et al., "Methods for Treating and Diagnosing Prostate Cancer," filed Sep. 13, 2018 (English translation) (27 pages).
Sheng, Jinghao, Thesis: "Gene Regulation of Angiogenin and Ribonuclease-4 and their biological functions," Zhejiang University, Chinese Doctoral Dissertations Full-text Database Medicine and Health Sciences, No. 4, pp. 54-84 (Apr. 2014) (34 pages).
Vanli et al., "Mechanism and Function of Angiogenin in Prostate Cancer," Chinese J. Biochem. Mol. Biol. 31(12):1261-1266 (Dec. 2015).

* cited by examiner

*Primary Examiner* — Sean E Aeder
(74) *Attorney, Agent, or Firm* — Clark & Elbing LLP

(57) ABSTRACT

The invention provides methods for treating and diagnosing prostate cancer, as well as related positions and kits.

27 Claims, 21 Drawing Sheets

Specification includes a Sequence Listing.

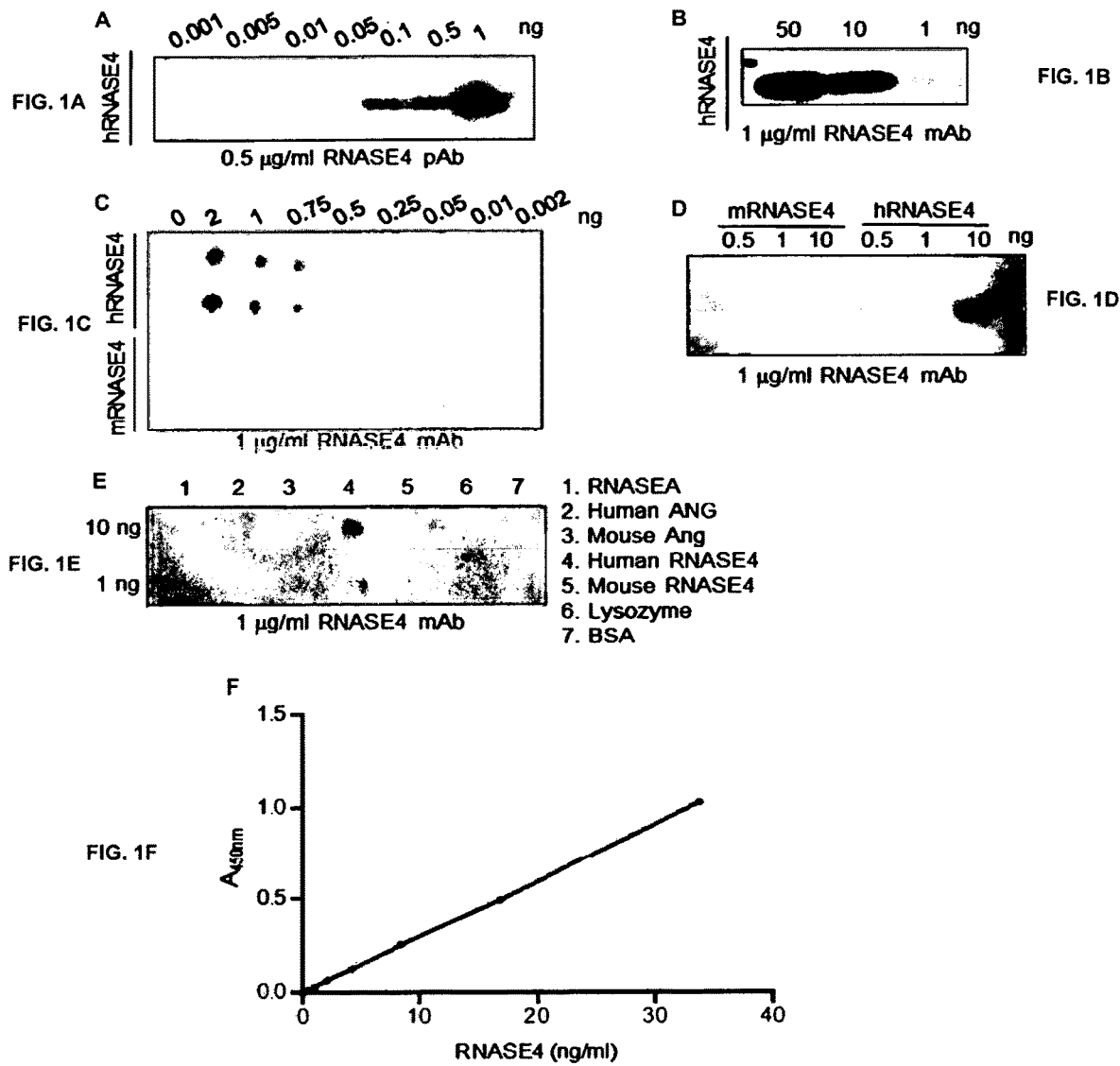
Sensitivity and specificity of RNASE4 polyclonal antibodies (pAb) and monoclonal antibodies (mAb)

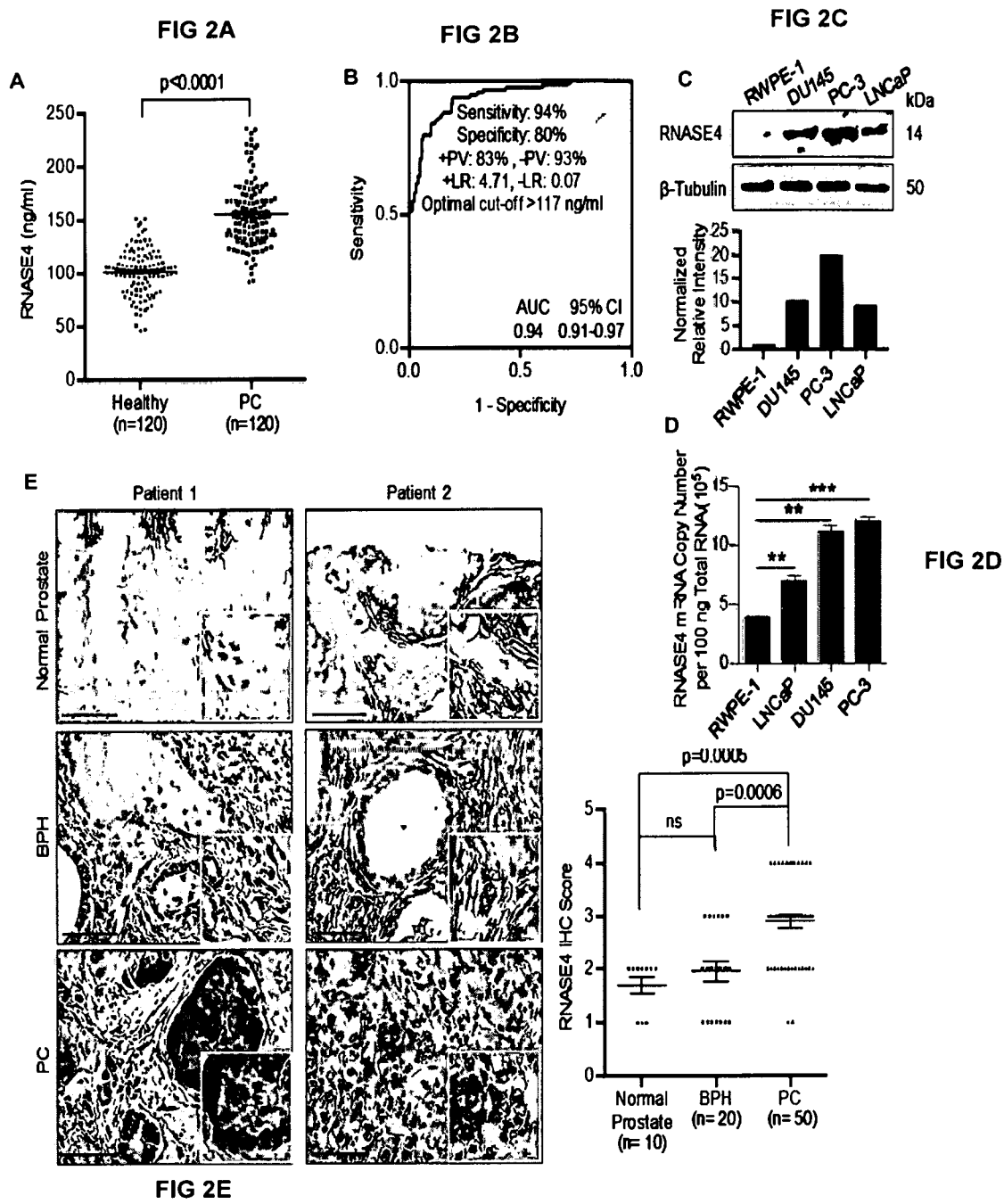
Up-regulation of RNASE4 in prostate cancer

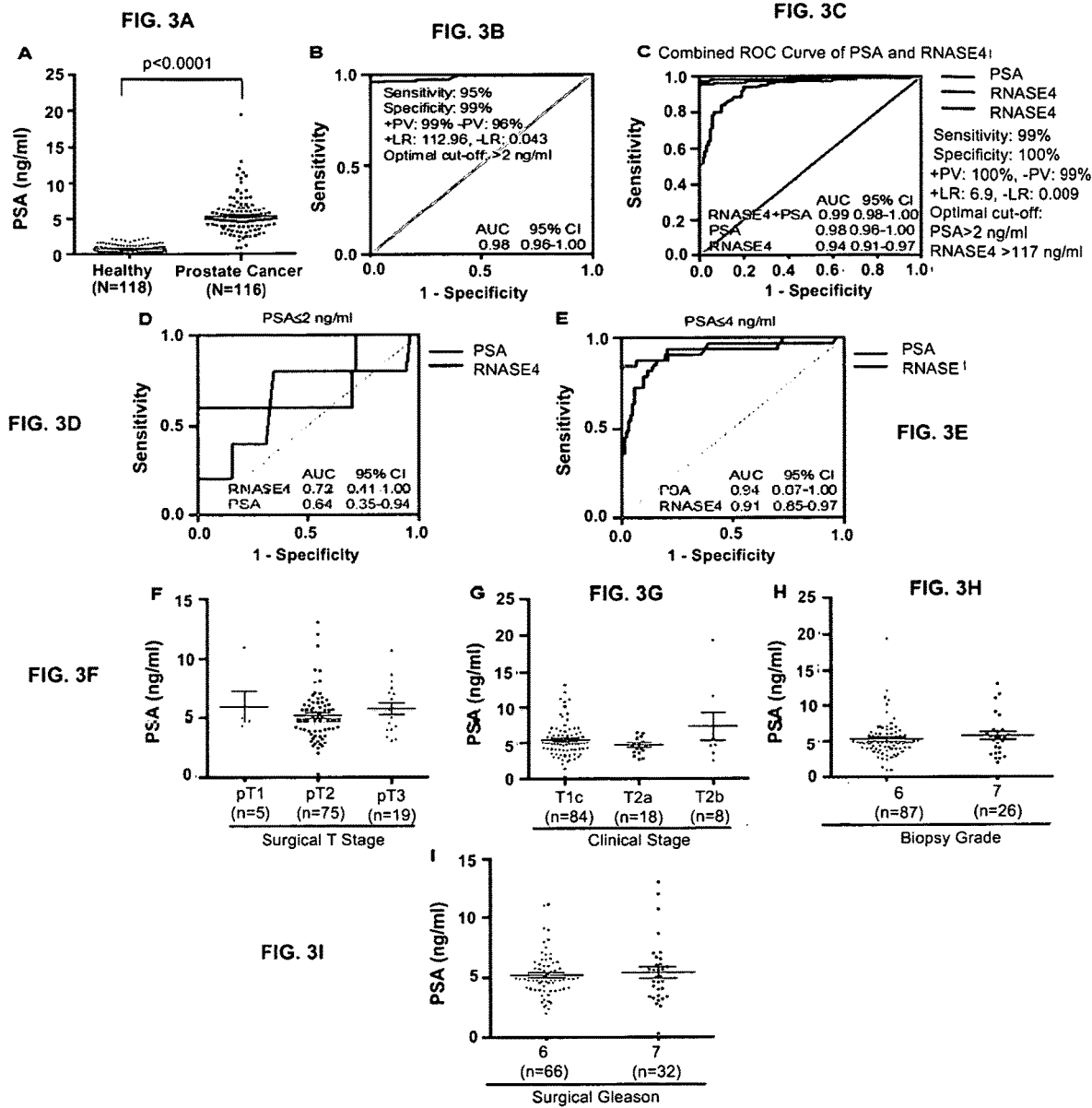
PSA level is elevated in the plasma of prostate cancer patients but not correlated with poor prognosis

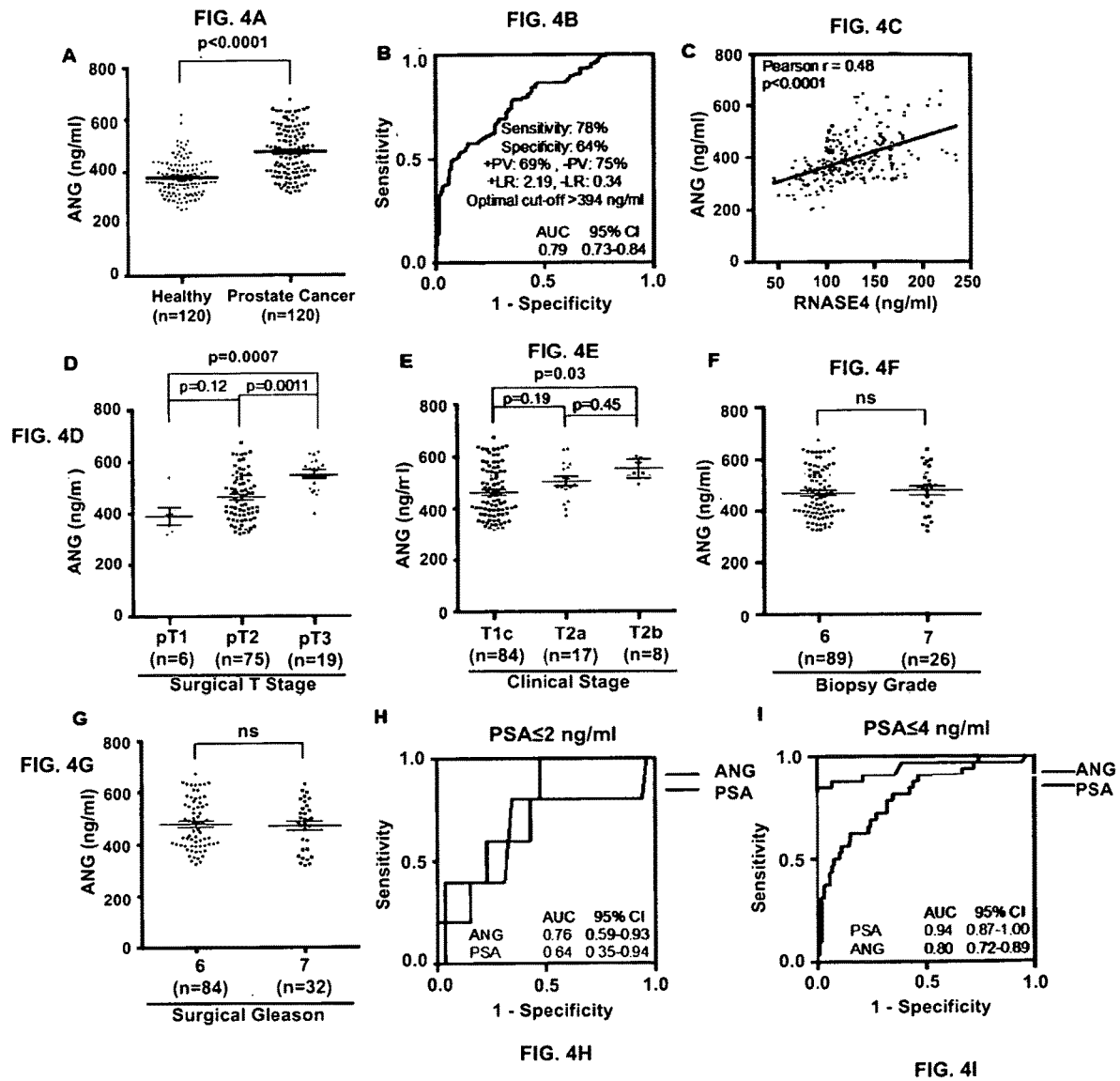
ANG level is elevated in the plasma of prostate cancer patients and is correlated only with surgical T stage

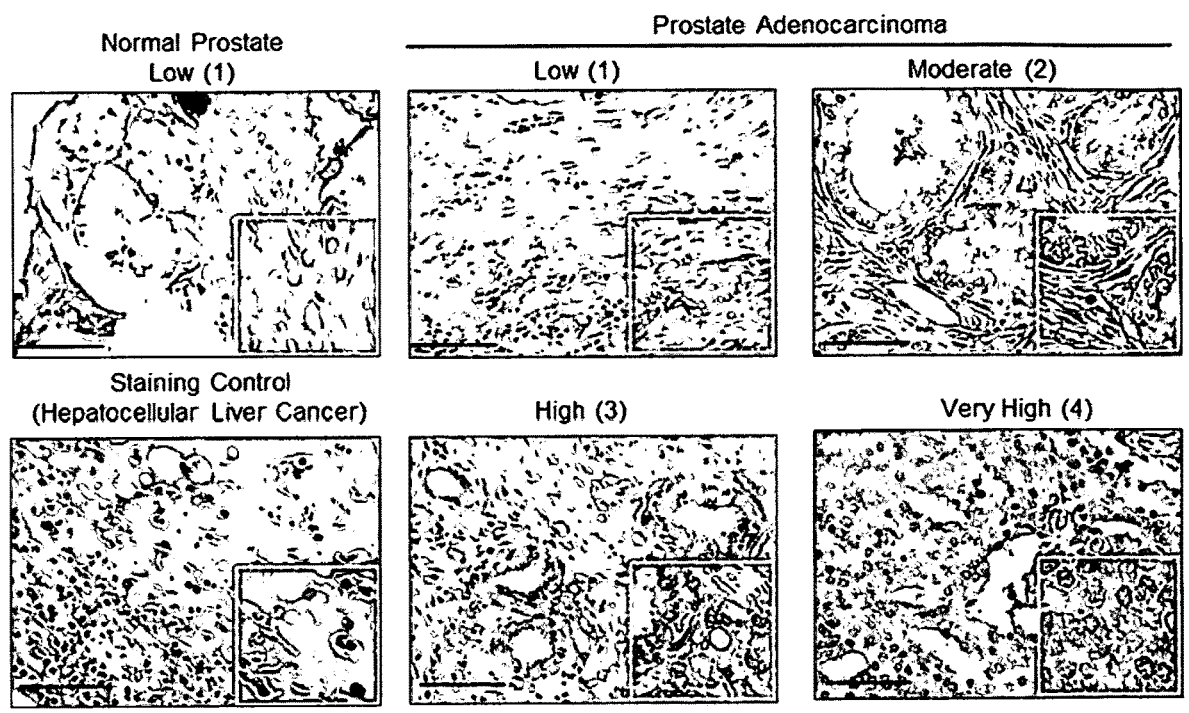
Figure 5. RNASE4 IHC scoring in tissue micro array

FIG. 6A

A  RNASE4 Expression in Bittner Multi-cancer Dataset

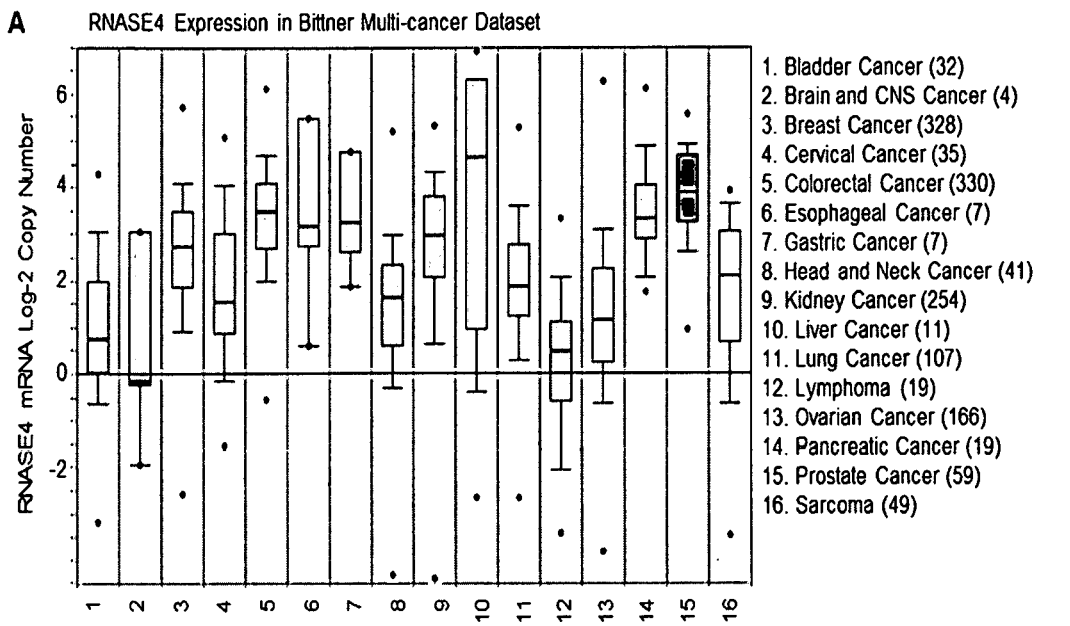

1. Bladder Cancer (32)
2. Brain and CNS Cancer (4)
3. Breast Cancer (328)
4. Cervical Cancer (35)
5. Colorectal Cancer (330)
6. Esophageal Cancer (7)
7. Gastric Cancer (7)
8. Head and Neck Cancer (41)
9. Kidney Cancer (254)
10. Liver Cancer (11)
11. Lung Cancer (107)
12. Lymphoma (19)
13. Ovarian Cancer (166)
14. Pancreatic Cancer (19)
15. Prostate Cancer (59)
16. Sarcoma (49)

B  RNASE4 Expression in Su Multi-cancer Dataset

FIG. 6B

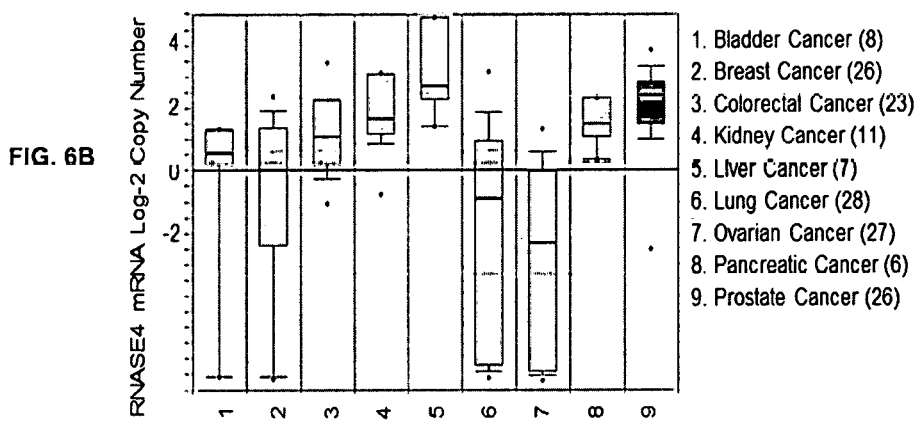

1. Bladder Cancer (8)
2. Breast Cancer (26)
3. Colorectal Cancer (23)
4. Kidney Cancer (11)
5. Liver Cancer (7)
6. Lung Cancer (28)
7. Ovarian Cancer (27)
8. Pancreatic Cancer (6)
9. Prostate Cancer (26)

Prostate Cancer

| Multi-cancer Dataset | Fold change | P-value | n |
|---|---|---|---|
| Bittner | 3.88 | 5.58E-17 | 59 |
| Su | 2.40 | 1.70E-11 | 26 |

**Bioinformatics analyses of *RNASE4* expression level in human cancers**

Gain of *RNASE4* and *AXL gene copy numbers* is associated with poor outcome of prostate cancer

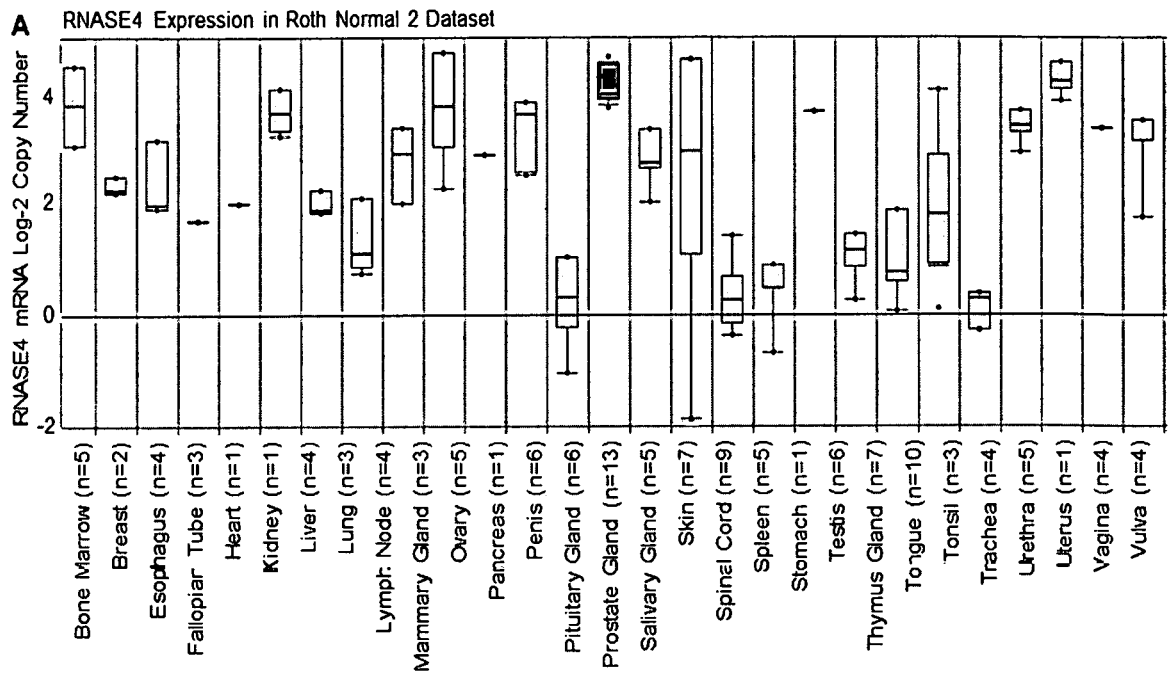
Bioinformatics analyses of *RNASE4* mRNA level in normal human organs RNASE4 protein levels in the plasma tissues of prostate cancer patients are correlated with poor prognosis and high risk of metastasis

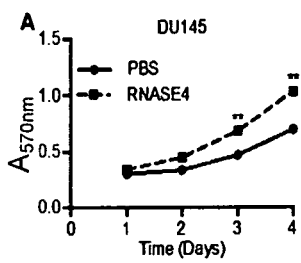
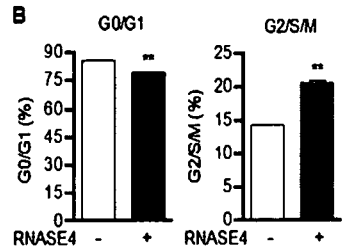
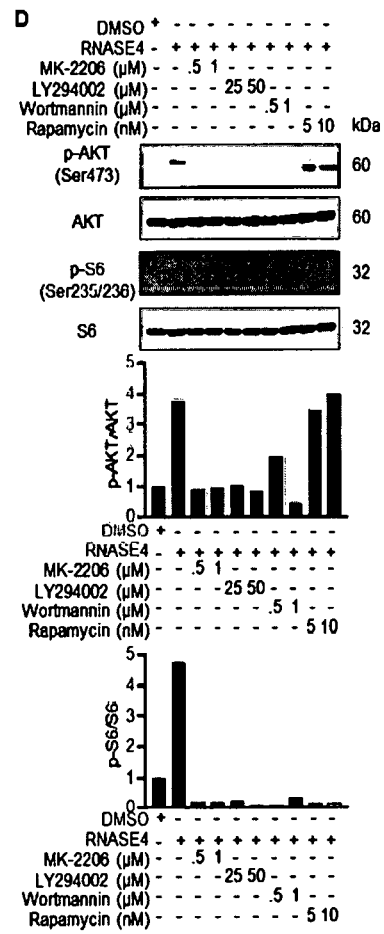
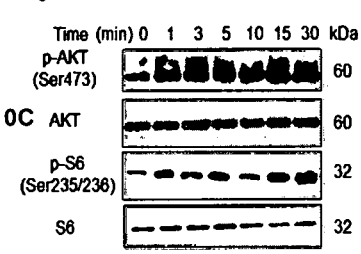
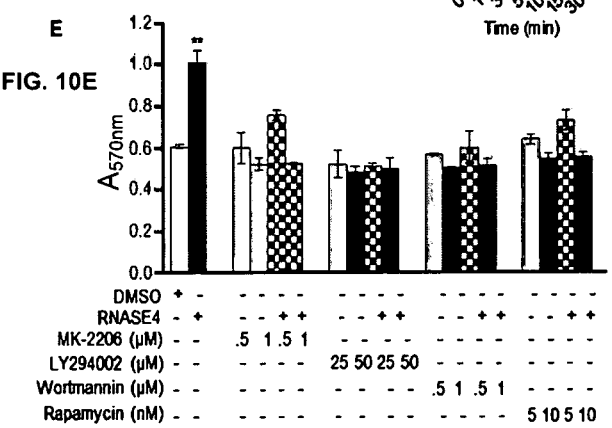
RNASE4 induces prostate cancer cell proliferation and phosphorylation of AKT and S6

RNASE4 induces PC-3 cell proliferation and phosphorylation of AKT and S6

FIG. 12A
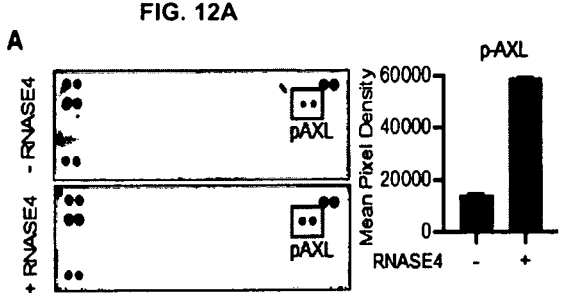
FIG. 12B
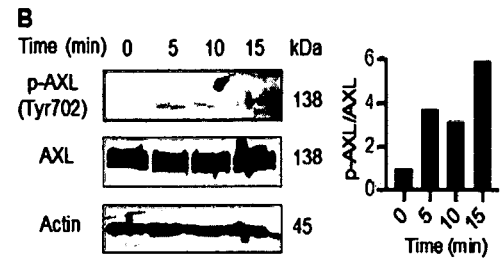
FIG. 12C
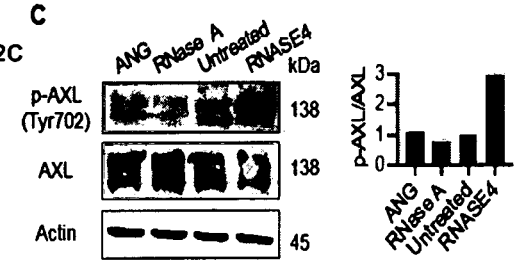
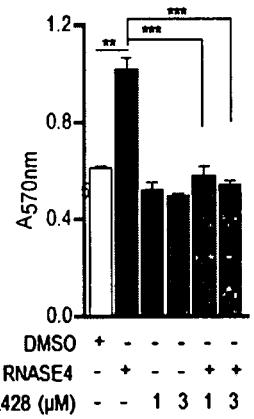
FIG. 12D
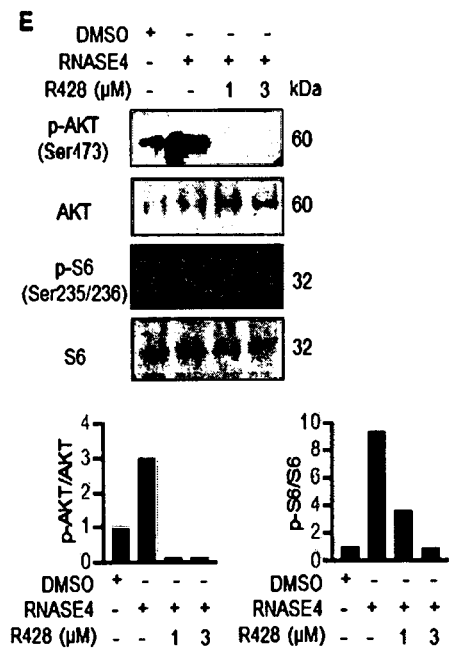
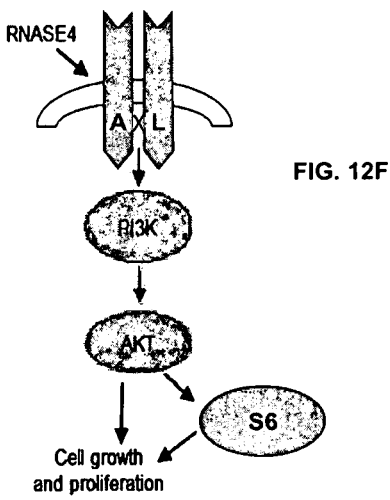
FIG. 12F
RNASE4 induces AXL phosphorylation

FIG. 13A  FIG. 13B  FIG. 13C
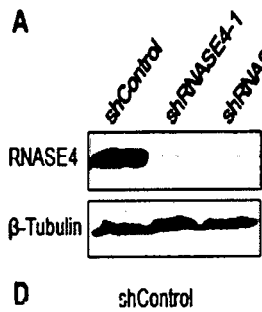
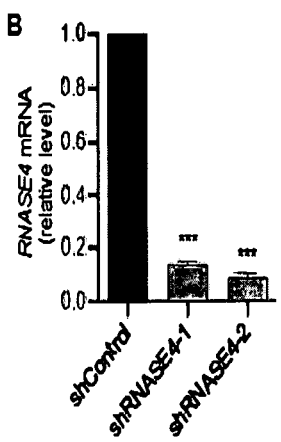
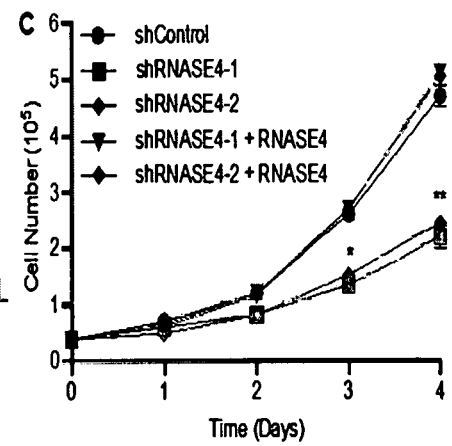
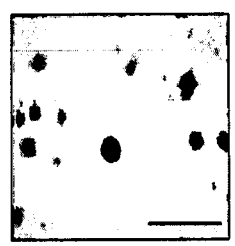
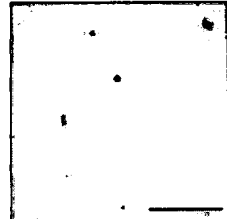
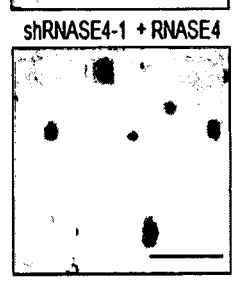
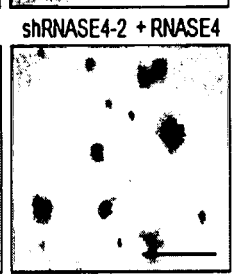
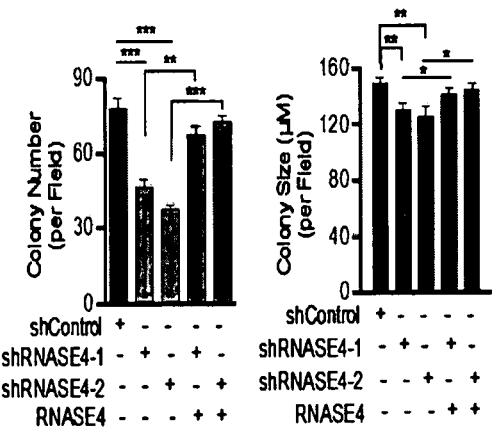
FIG. 13D
*RNASE4* knockdown reduces prostate cancer cell proliferation *in vitro* and colony formation in soft agar FIG. 14A  FIG. 14B  FIG. 14C
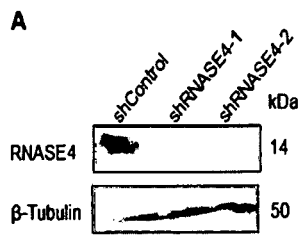
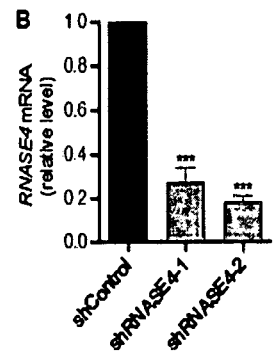
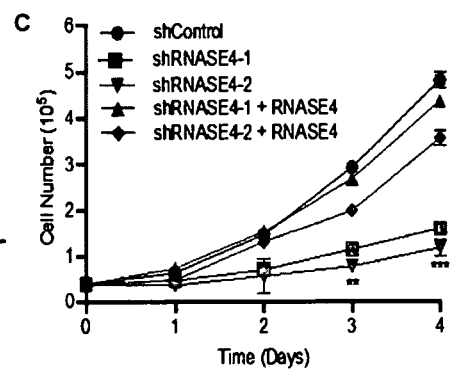
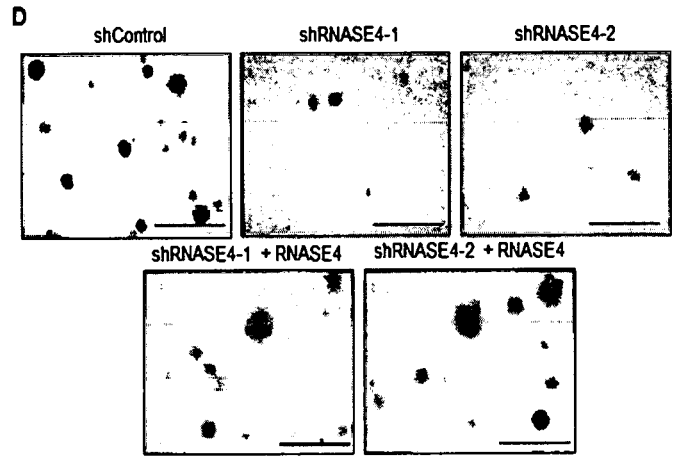
FIG. 14D
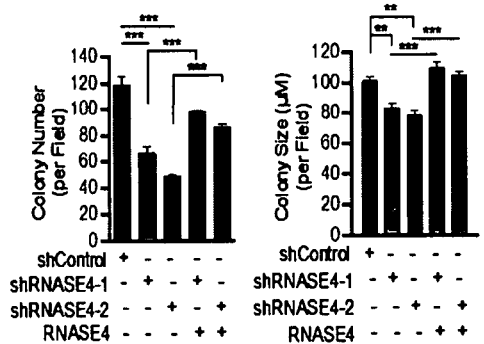
*RNASE4* knockdown inhibits DU145 cell proliferation *in vitro* and colony formation in soft agar FIG. 15A  FIG. 15B  FIG. 15C
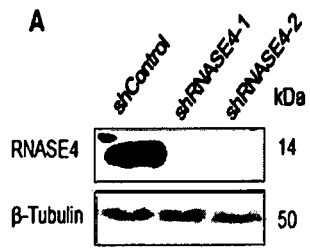
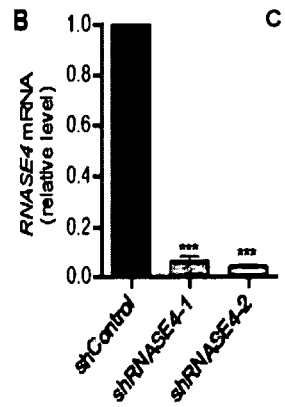
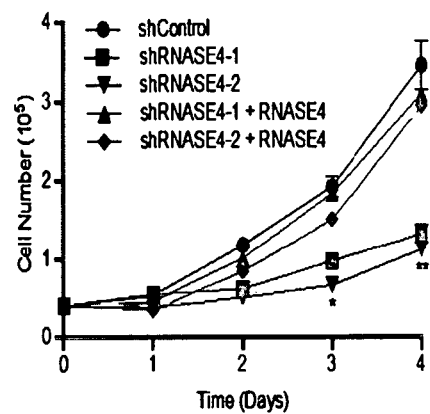
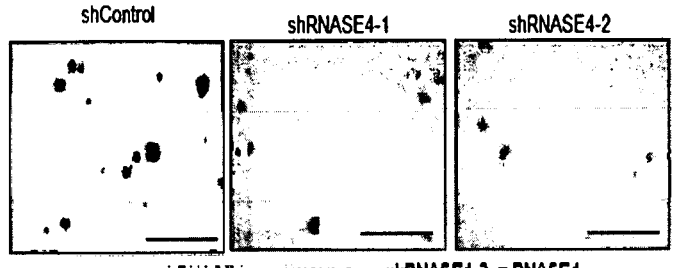
FIG. 15D
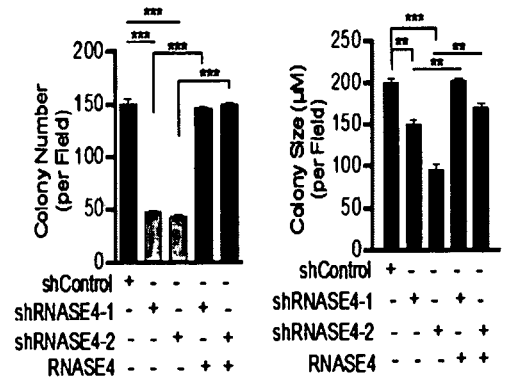
*RNASE4* knockdown inhibits LNCaP cell proliferation *in vitro* and colony formation in soft agar

*RNASE4* knockdown slows down xenograft growth of human prostate cancer cell tumors in athymic mice FIG. 17A
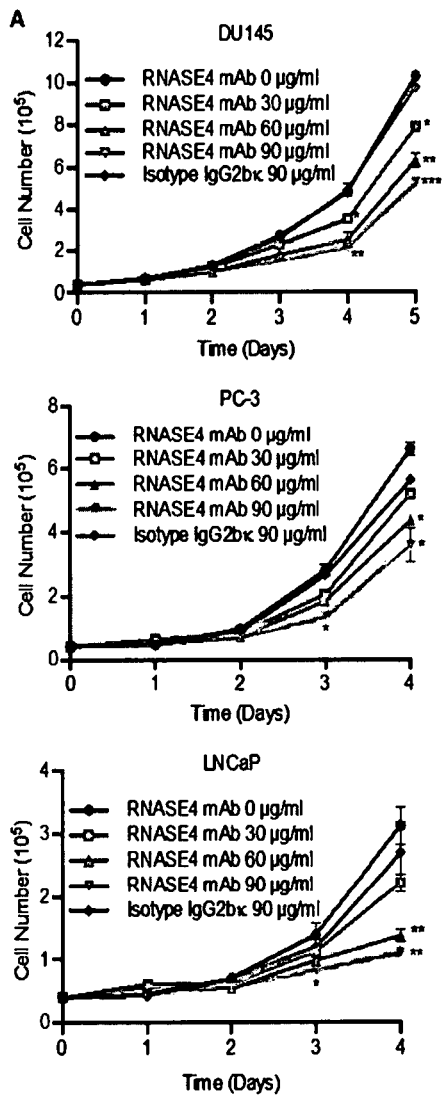
FIG. 17B
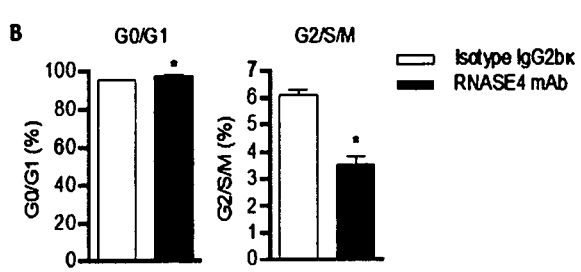
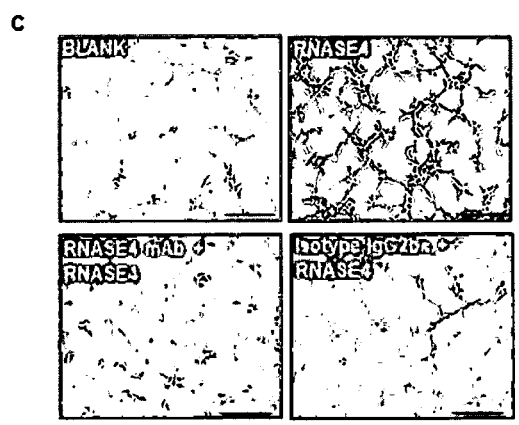
FIG. 17C
RNASE4 mAb inhibits prostate cancer cell proliferation and RNASE4-induced angiogenesis

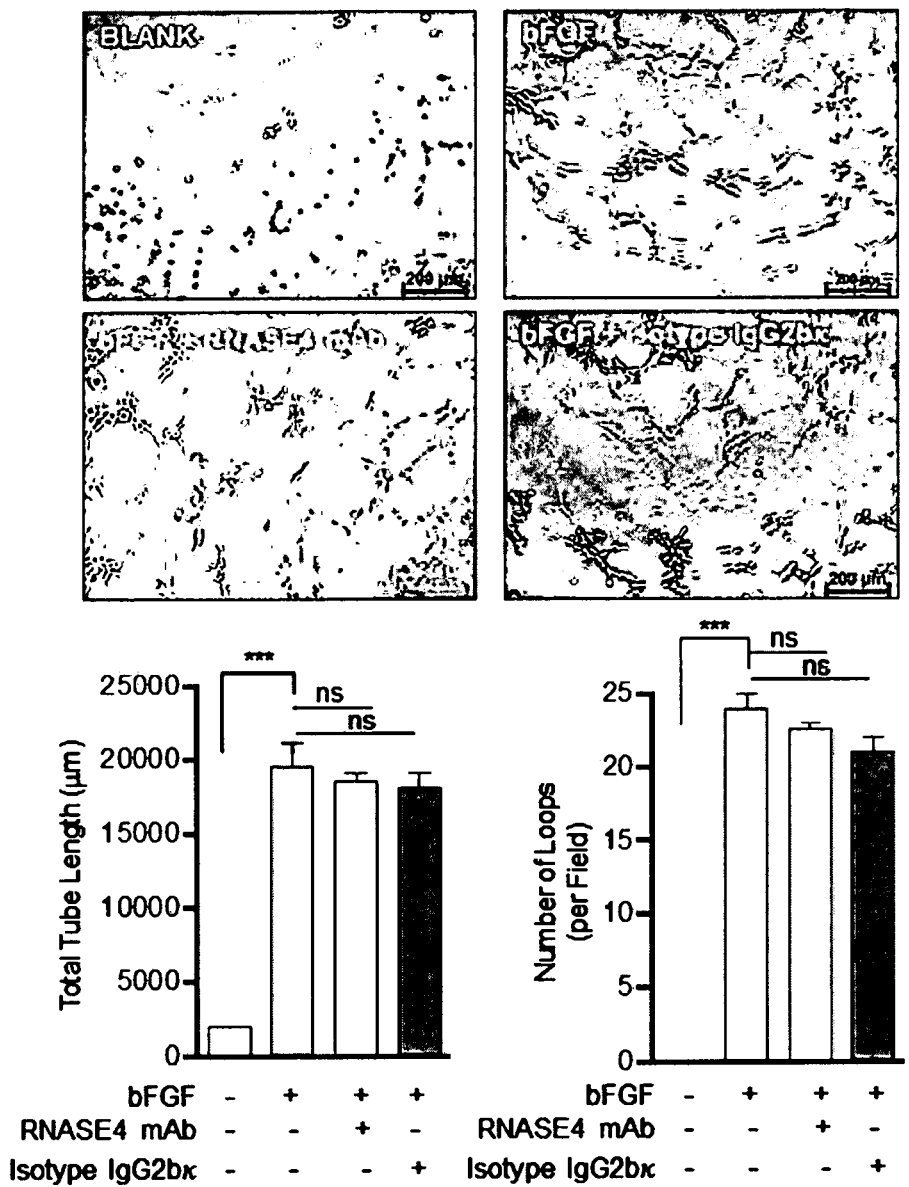
Figure 18. RNASE4 mAb does not inhibit basic FGF (bFGF)-induced angiogenesis

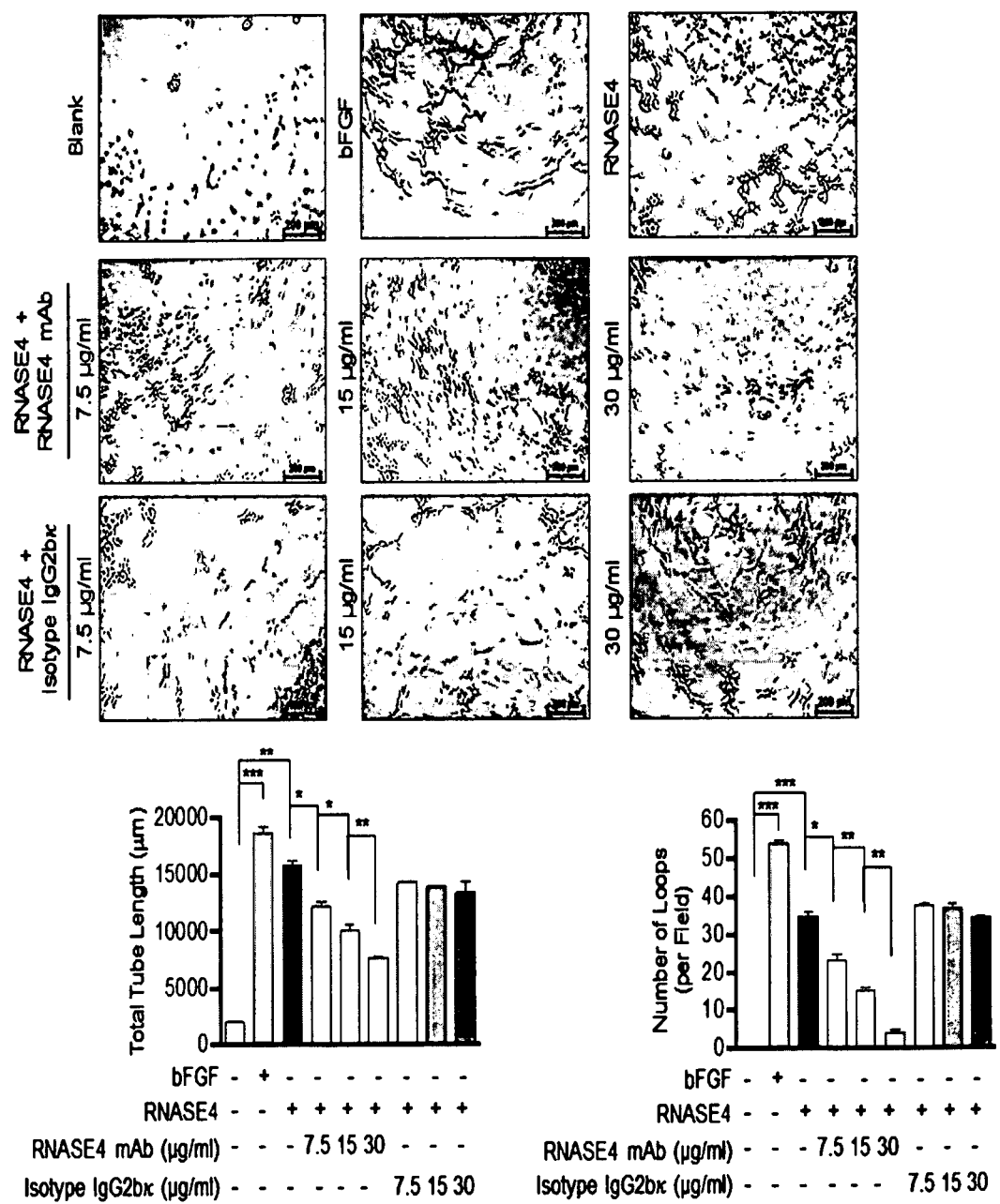
Figure 19. RNASE4 mAb inhibits RNASE4-mediated angiogenesis in a dose-dependent manner

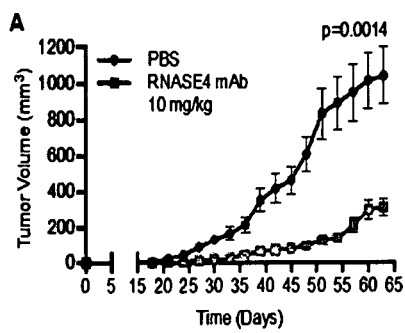
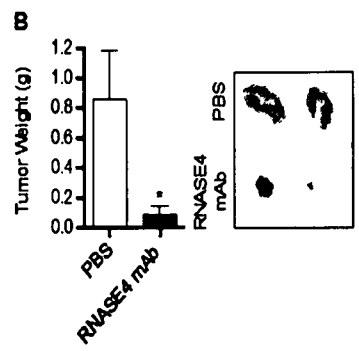
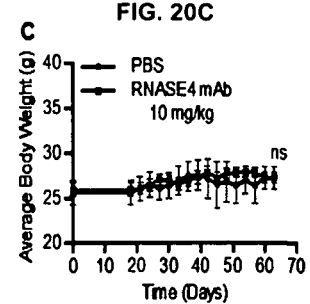
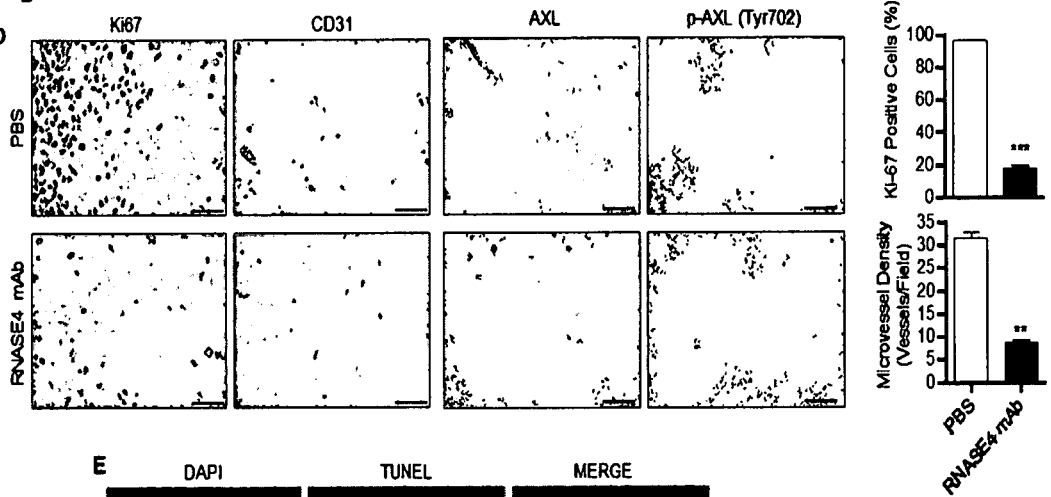
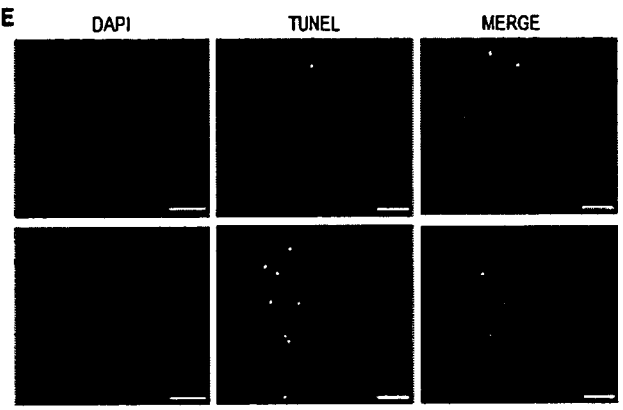
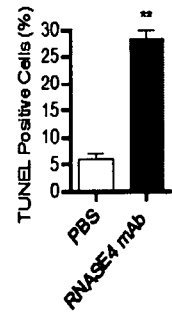
RNASE4 mAb inhibits the establishment of xenograft human prostate cell tumors in athymic mice

RNASE4 mAb inhibits the growth of established xenograft human prostate cell tumors in athymic mice

SEQUENCE LISTING

<160> NUMBER OF SEQ ID NOS: 7

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
agaagcgggt gagaaacaa                                                  19

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
agtagcgatc actgccacct                                                 20

<210> SEQ ID NO 3
<211> LENGTH: 19
<212> TYPE: DNA
<213> ORGANISM: Artificial Sequence
<220> FEATURE:
<223> OTHER INFORMATION: Synthetic Construct

<400> SEQUENCE: 3
tgaacgggaa gctcactgg                                                  19

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
tccaccaccc tgttgctgta                                                 20

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct

<400> SEQUENCE: 5
atctcgcttg ggcgagagta agta                                            24

<210> SEQ ID NO 6
<211> LENGTH: 21
<212> TYPE: DNA
<213> ORGANISM: Artificial Sequence
<220> FEATURE:
<223> OTHER INFORMATION: Synthetic Construct

<400> SEQUENCE: 6
acctgtcagg gaggcattaa a                                               21

<210> SEQ ID NO 7
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 7
caaagagata tggagacata a                                        21
```

METHODS FOR TREATING AND DIAGNOSING PROSTATE CANCER

SEQUENCE LISTING

The instant application contains a Sequence Listing which has been submitted electronically in ASCII format and is hereby incorporated by reference in its entirety. Said ASCII copy, created Mar. 13, 2020, is named 00398-547002_Sequence_Listing_03.13.20_ST25 and is 1,633 bytes in size.

FIELD OF THE INVENTION

The invention relates to therapeutic and diagnostic methods for prostate cancer.

BACKGROUND OF THE INVENTION

Prostate cancer is common in American men. The incidence rate is expected to grow with the aging population (Miller et al., CA: A Cancer J. Clin. 66(4):271-289, 2016). Diagnostic tools most commonly used in prostate cancer are the prostate specific antigen (PSA) test, digital rectal exam, and ultrasound in combination with guided biopsy and histopathological Gleason grading (Klotz et al., Nat. Rev. Clin. Oncol. 11(6):324-334, 2014). Of these, only PSA can be classified as a biomarker but is limited in predicting prognosis, which leads to either over-treatment or under-treatment (Barlow et al., Cancer Cell 24(3):e401, 2013; Barry, N. Engl. J. Med. 360(13):1351-1354, 2009; Schroder et al., N. Engl. J. Med. 360(13):1320-1328, 2009). Furthermore, PSA is not a biomarker specific for prostate cancer as its level is also elevated in prostatitis and in benign prostatic hyperplasia (BPH) (Chang et al., Nat. Rev. Clin. Oncol. 11(6):308-323, 2014). Several other biomarkers have been discovered such as PSA derivatives and prostate cancer antigen 3 (Prensner et al., Sci. Transl. Med. 4(127):127rv3, 2012). However, multiple studies have failed to demonstrate independent values of these markers to predict cancer progression (Hoffman, N. Engl. J. Med. 365(21):2013-2019, 2011; Tosoian et al., J. Urol. 183(2):534-538, 2010). It is thus necessary to identify novel noninvasive biomarkers that can provide a higher degree of specificity for detecting aggressiveness and for predicting progression of prostate cancer.

There also are unmet clinical needs for novel therapies for prostate cancer, especially for patients with advanced or aggressive cancers. Prostate cancer deaths are typically the result of aggressive metastases that are unresponsive to androgen deprivation therapy (Walsh et al., N. Engl. J. Med. 357(26):2696-2705, 2007).

Human pancreatic ribonucleases are a large superfamily of enzymes with diverse functions (Cho et al., Genomics 85(2):208-220, 2005), including growth and survival, angiogenesis, neurogenesis, immune-regulation, and host defense (Beintema et al., Cell Mol. Life Sci. 54(8):825-832, 1998; Di Liddo et al., Mol. Med. Rep. 3(1):127-132, 2010; Dyer et al., Mol. Divers. 10(4):585-597, 2006; Harder et al., J. Biol. Chem. 277(48):46779-46784, 2002; Hooper et al., Nat. Immunol. 4(3):269-273, 2003; D'Alessio et al., Trends Biochem. Sci. 16(3):104-106, 1991; Kishimoto et al., Oncogene 24(3):445-456, 2005). Among the 13 members of this superfamily, ribonuclease 4 (RNASE4) is unique and has two distinct features. In particular, it has the most conserved amino acid sequence among vertebrate species (94% identity among human, bovine, mouse, and porcine species) (Rosenberg et al., Nucl. Acids Res. 23(21):4290-4295, 1995; Zhou et al., Eur. J. Biochem. 217(1):401-410, 1993; Hofsteenge et al., Cell Mol. Life Sci. 54(8):804-810, 1998; Seno et al., Biochim. Biophys. Acta Gene Struct. Expr. 1261(3): 424-426, 1995), and has the strictest substrate specificity (only at the 3' side of uridine) (Terzyan et al., J. Mol. Biol. 285(1):205-214, 1999; Li et al., Angiogenesis 16(2):387-404, 2013). These features suggest that RNASE4 may have a unique biological role.

SUMMARY OF THE INVENTION

The invention includes methods of treating or preventing prostate cancer in a subject, such as a human patient. These methods include administering to the subject an inhibitor of ribonuclease 4 (RNASE4) (e.g., a small molecule, an antibody or an antigen binding fragment thereof (e.g., a polyclonal antibody, a monoclonal antibody, or a single chain antibody), an antisense RNA, or an shRNA).

The invention also includes methods for identifying subjects, such as human subjects, having or at risk of prostate cancer. These methods include including determining the level of expression of RNASE4 in a sample obtained from a subject, wherein an increased level of expression of RNASE4 in the sample, as compared to a reference level, identifies the subject as having prostate cancer. The methods can, in some examples, optionally be carried out to differentiate between benign prostate hyperplasia (BPH) and prostate cancer in the subject, and the reference level in such methods can optionally be characteristic of BPH. In other examples, the methods can optionally be carried out in determination of whether to carry out a needle biopsy on the subject.

Also included in the invention are methods for assessing the prognosis of a subject having prostate cancer, monitoring the efficacy of treatment in the subject, or selecting therapy for the subject. These methods can include determining the level of expression of RNASE4 in a sample obtained from the subject, wherein an increased level of expression of RNASE4 in the sample, as compared to a reference level, indicates a subject having a poor prognosis, that the treatment is not having a beneficial effect on the subject, or that it may be beneficial to treat the subject with an inhibitor of RNASE4, respectively. In various examples, the method is carried out to assess the prognosis of the subject, and the assessing of the prognosis includes determining the risk of metastasis, level of disease aggressiveness, tumor grade, or cancer stage.

The invention also provides methods for determining the stage, sub-stage, or risk level of prostate cancer in a subject (e.g., TX, T0, T1 (T1a, T1b, or T1c), T2 (T2a, T2b, or T2c), T3 (T3a, T3b, or T3c), T4, NX, N0, N1, MX, M0, M1 (M1a, M1b, or M1c), Gleason score (6 or lower, 7, 8, 9, or 10), Gleason Group (I, II, III, IV, or V), very low risk, low risk, intermediate risk, high risk, or very high risk). These methods include determining the level of expression of RNASE4 in a sample obtained from the subject with one or more reference samples (e.g., as described herein).

In the diagnostic methods described above, the sample obtained from the subject can be selected from the group consisting of a sample of whole blood, serum, plasma, and prostate tissue. Furthermore, the methods can further include determining the level of expression of prostate specific antigen (PSA) and/or angiogenin (ANG) in the sample. The levels of expression can be determined by assessing protein expression levels (e.g., by use of an immunoassay, such as an enzyme-linked immunosorbent assay (ELISA), optionally using an antibody or an antigen binding fragment thereof (e.g., a monoclonal antibody, a polyclonal antibody, or a single chain antibody) that is specific for RNASE4) or by assessing mRNA expression level (e.g., by qPCR, RNA-Seq, microarray analysis, gene expression profiling, or whole genome sequencing). The level of expression level of RNASE4 can optionally be increased or decreased by, e.g., about 0.1, 0.25, 0.5, 1, 2, 5, or 10 fold relative to the reference level, which optionally is the expression level in a sample from the subject prior to treatment, the level in a reference population, a pre-assigned level, the level in subjects having prostate cancer, the level in subjects having prostate cancer of a particular stage, or the level in subjects having BPH.

The diagnostic methods of the invention also can optionally include a step of treating the subject for prostate cancer, e.g., by administering a treatment for prostate cancer to the subject. Optionally, the treatment for prostate cancer includes an inhibitor of RNASE4 (e.g., a small molecule, an antibody or an antigen binding fragment thereof (e.g., a polyclonal antibody, a monoclonal antibody, or a single chain antibody), an antisense RNA, or an shRNA.

The invention also includes methods of inhibiting the growth of prostate cancer cells (e.g., prostate cancer cells in a subject), which involve contacting the prostate cancer cells with an RNASE4 inhibitor (e.g., an antibody or an RNASE4 binding fragment thereof).

Further, the invention includes methods of inhibiting angiogenesis in a subject having prostate cancer, which involve administering an RNASE4 inhibitor (e.g., an antibody or an RNASE4 binding fragment thereof) to the subject.

Also included in the invention are kits for identifying subjects having or being at risk for prostate cancer. The kits can include (a) one or more polypeptides (e.g., an antibody against RNASE4 or an RNASE4 binding fragment thereof) or polynucleotides (e.g., a probe or one or more primers specific for RNASE4 nucleotide sequences) that can be used to determine the level of RNASE4 protein or nucleic acid in a sample, and, optionally (b) instructions for using the one or more polypeptides or polynucleotides in an assay for the determination. The kits can further optionally include one or more control polypeptides or polynucleotides.

An "antagonist" or "inhibitor" is a compound or agent that inhibits or reduces the biological activity of a target molecule (e.g., RNASE4). Antagonists include, e.g., antibodies or antigen-binding fragments thereof, peptides, nucleic acid molecules (e.g., antisense molecules, shRNA, etc.), and small molecules. A "blocking" antibody or an "antagonist" antibody is one that inhibits or reduces biological activity of the antigen to which it binds. The term "RNASE4 inhibitor" refers to a molecule that decreases, blocks, inhibits, prevents, abrogates, or interferes with the activity of RNASE4 (e.g., RNASE4-induced prostate cell proliferation or angiogenesis).

The term "antibody" herein is used broadly to encompass various antibody structures including, for example, monoclonal antibodies, polyclonal antibodies, monospecific antibodies, multispecific antibodies (e.g., bispecific antibodies), single chain antibodies, and antibody fragments that exhibit a desired antigen-binding activity. Antibodies can optionally be chimeric, human, or humanized. DNA-encoded monoclonal antibodies can also be used. "Antibody fragments" include a portion of an intact antibody, such as the antigen-binding region of an antibody. Examples of antibody fragments include Fab, Fab', F(ab')2, and Fv fragments. Single-chain antibodies can also be referred to as antibody fragments.

The term "small molecule" refers to any molecule with a molecular weight of about 2000 daltons or less, e.g., about 500 daltons or less.

The "level" of RNASE4 herein can be the detectable amount of RNASE4 polynucleotide (e.g., mRNA) and/or amino acid product or protein present in a sample. The level of RNASE4 can reference the amount of expression of the RNASE4 polynucleotide or protein, where "expression" generally refers to a process in which gene-encoded information is transcribed into RNA, which is processed into mRNA, which is translated into protein. "Increased expression," "increased expression level," or "increased levels" refers to an increased expression or increased levels of a biomarker in a sample from a test subject relative to a control, such as a matched sample from one or more individuals who do not have prostate cancer, an internal control (e.g., a housekeeping biomarker), or a median expression level of the biomarker in samples from a group/population of individuals (e.g., patients; also see below). "Decreased expression," "decreased expression level," or "decreased levels" in turn refers to a decrease expression or decreased levels of a biomarker in a sample from a test subject relative to a control, such as a matched sample from one or more individuals who do not have prostate cancer, an internal control (e.g., a housekeeping biomarker), or a median expression level of the biomarker in samples from a group/population of individuals (e.g., patients; also see below). In some instances, reduced expression is little or no expression.

The term "sample" or "test sample" as used herein, refers to a composition that is obtained or derived from a subject (e.g., a test subject), and which contains or is suspected to contain, e.g., RNASE4 polynucleotide and/or protein. Samples include, e.g., blood (e.g., whole blood, serum, plasma, or platelets), cell samples, tissue samples (e.g., prostate biopsies, prostate tumors, metastatic tumors, and tissues or fluids local to the prostate), primary or cultured cells, cell supernatants, cell lysates, lymph fluid, synovial fluid, seminal fluid, urine, cerebrospinal fluid, saliva, sputum, tears, perspiration, mucus, tumor lysates, and tissue culture medium, tissue extracts such as homogenized tissue, tumor tissue, cellular extracts, and combinations thereof.

A "reference sample" or "control sample" is a sample that is used for the purpose of comparison to a test sample. In various examples, a reference sample is obtained from one or more individuals who do not have prostate cancer, or from a test subject before, during, or after treatment. "Reference levels" or "control levels" of RNASE4 or expression thereof can optionally be based on levels obtained from "reference samples" or "control samples."

The term "about" as used herein refers to the usual error range for a respective value as readily assessed by those of skill in the art. Thus, reference to "about" a value or parameter herein includes examples that are directed to that value or parameter, as well as values or parameters within the error range.

The invention provides several advantages. For example, although PSA screening has resulted in a decrease in prostate cancer-related deaths, it also has led to over-treatment, which unnecessarily affects the quality of life of many patients. According to the present invention, RNASE4 can be used as a diagnostic and prognostic marker for prostate cancer, and facilitates distinguishing prostate cancer from benign prostate hyperplasia (BPH) and prediction of aggressiveness of the disease. Thus, the invention can be used to more accurately diagnose prostate cancer, to avoid unnecessary treatment. In addition, RNASE4 screening shows improvements over PSA with respect to early stage screening, and can be used in combination with PSA screening to improve the accuracy of PSA screening. The invention also provides RNASE4 as a new therapeutic target for the treatment and prevention of prostate cancer. In addition, the invention includes use of the therapeutics described herein for preventing and/or treating the diseases and conditions described herein, as well as the use of these therapeutics for the preparation of medicaments for these purposes.

Other features and advantages of the invention will be apparent from the following detailed description, the drawings, and the claims.

BRIEF DESCRIPTION OF THE DRAWINGS

FIGS. 1A-F. Sensitivity and specificity of RNASE4 polyclonal antibodies (pAb) and mAb. (A) Detection of human RNASE4 protein by RNASE4 pAb in immunobloting. At 0.5 µg/ml, RNASE4 pAb was able to detect as low as 50 pg RNASE4. (B) Detection of human RNASE4 protein by RNASE4 mAb in immunoblotting. At 1 RNASE4 mAb was able to detect as low as 1 ng RNASE4. (C) Detection of human and mouse RNASE4 protein by RNASE4 mAb in dot blotting. At 1 RNASE4 mAb was able to detect 0.5 ng human RNASE4 but not 2 ng mouse RNASE4 in dot blotting. (D) Detection of human and mouse RNASE4 protein by RNASE4 mAb in immunoblotting. At 1 µg/ml, RNASE4 mAb was able to detect 1 ng human RNASE4 but not 10 ng mouse RNASE4 in immunoblotting. (E) Detection of RNASEA, human and mouse ANG, human and mouse RNASE4, lysozyme, and BSA by RNASE4 mAb in dot blotting. At 1 µg/ml, RNASE4 mAb was able to detect 1 and 10 ng human RNASE4, but not anything else. (F) A typical standard curve of RNASE4 sandwich ELISA using the above RNASE4 pAb and mAb.

FIGS. 2A-E. Up-regulation of RNASE4 in prostate cancer. (A) RNASE4 protein levels in the plasma of healthy control subjects (n=120) and prostate cancer (PC) patients (n=120). RNASE4 amounts were determined by ELISA. Each dot represents an individual sample. Lines mark the median values and interquartile ranges. (B) Receiving Operating Characteristic (ROC) curve analysis. AUC, area under the curve; +PV, positive predictive value; −PV, negative predictive value; +LR, positive likelihood ratio; −LR, negative likelihood ratio. (C) Immunoblot analysis of RNASE4 from normal prostate epithelial cell line RWPE-1 and prostate cancer cell lines DU145, PC-3, and LNCaP. Top panel, immunoblots; bottom panel, quantification of RNASE4 protein levels by Image J using Tubulin as loading controls. (D) RNASE4 mRNA copy numbers in 100 ng total RNA of normal prostate and cancer cell lines determined by qRT-PCR. $P \leq 0.01$ and *$P \leq 0.001$, by unpaired two-tailed Student's t test. (E) IHC analysis of RNASE4 in tissue micro array. Left panels, two sets of representative images of prostate cancer, benign prostate hyperplasia (BPH) and normal prostate tissues, scale bars=50 µm; right panel, semi-quantitative score of RNASE4 in prostate cancer (n=50), BPH (n=20), and normal prostate (n=10) tissues. Data were analyzed by ANOVA using Dunnett's multiple comparison test. Each dot represents score of an individual tissue sample. The horizontal lines in the plots represent the median values and the interquartile ranges.

FIGS. 3A-I. PSA level is elevated in the plasma of prostate cancer patients but not correlated with poor prognosis. (A) PSA levels in plasma samples of healthy control subjects (n=120) and prostate cancer patients (n=120). Each dot represents an individual sample. Lines mark the median values and interquartile ranges. (B) Operating Characteristic Curve (ROC) analysis. AUC, area under the curve; +PV, positive predictive value; −PV, negative predictive value; +LR, positive likelihood ratio; −LR, negative likelihood ratio. (C) Combined ROC curve analysis of PSA and RNASE4 showed improved sensitivity and specificity at cut-off values 2 ng/ml and 117 ng/ml, respectively. Data shown are means±SEM. (D and E) ROC curve analyses of PSA and RNASE4 for patients with PSA≤2 ng/ml (D) and PSA≤4 ng/ml (E). (F-I) Lack of correlation of plasma PSA level with tumor surgical T-stage (F), clinical stage (G), biopsy grade (H), and surgical Gleason (I). No significant differences were found by one-way ANOVA (F and G) and two-tailed Student's t test (A, H, and I) analyses.

FIGS. 4A-I. ANG level is elevated in the plasma of prostate cancer patients and is correlated only with surgical T stage. (A) Levels of ANG protein in the plasma healthy control subjects (n=120) and prostate cancer patients (n=120). ANG amounts were determined by ELISA. Each dot represents an individual sample. Lines mark the median values and interquartile ranges. (B) Operating Characteristic Curve (ROC) analysis. AUC, area under the curve; +PV, positive predictive value; −PV, negative predictive value; +LR, positive likelihood ratio; −LR, negative likelihood ratio. (C) Correlation between RNASE4 and ANG in all plasma samples (n=240). (D-G) Plasma ANG levels in prostate cancer patients stratified by surgical T stage (D), clinical stage (E), biopsy grade (F), and surgical Gleason (G). Statistically significant differences were found only between pT1 and pT3, pT2 and pT3 (D), and between T1c and T2b (E). (H and I) ROC curve analyses of ANG and PSA for patients with PSA≤2 ng/ml (H) and PSA≤4 ng/ml (I). Statistical analyses used were one-way ANOVA (D and E) and two-tailed Student's t test (A, F, and G). ns=not significant.

FIG. 5. RNASE4 IHC scoring in tissue micro array. A semi-quantitative scoring scale was used to score staining density of RNASE4 in the tissue microarray. IHC score is indicated in parentheses. Staining was ranked from 1 (low) to 4 (very high). RNASE4 staining was low in normal prostate tissue. Hepatocellular liver cancer tissue was used as positive staining control. Scale bars=50 µm.

FIGS. 6A-C. Bioinformatics analyses of RNASE4 expression level in human cancers. (A) RNASE4 mRNA level in different human cancers from Bittner Multi-cancer dataset. (B) RNASE4 mRNA level in different human cancers from Su multi-cancer dataset. The boxes represent the medians (black middle line) limited by the 25th (Q1) and 75th (Q3) percentiles. The whiskers are the upper and lower adjacent values, which are the most extreme values within Q3+1.5(Q3-Q1) and Q1-1.5(Q3-Q1), respectively. The number of patient samples is indicated in parentheses. (C) P-values and fold changes of RNASE4 overexpression in prostate cancer from the two datasets.

FIGS. 8A-B. Bioinformatics analyses of RNASE4 mRNA level in normal human organs. (A) Organs with higher RNASE4 mRNA level than the average of all human organs. The boxes represent the medians (black middle lines) limited by the 25th (Q1) and 75th (Q3) percentiles. The whiskers are the upper and lower adjacent values, which are the most extreme values within Q3+1.5(Q3-Q1) and Q1-1.5(Q3-Q1), respectively. The number of patient samples is indicated in parentheses. The horizontal line at 0 marks average RNASE4 mRNA level of all organs. RNASE4 mRNA level in the prostate gland is 4.33 fold higher compared to other healthy organs ($p=6.21 \times 10^{-23}$). (B) P-values and fold changes of RNASE4 mRNA in the 7 healthy human organs with the highest expression.

FIGS. 10A-E. RNASE4 induces prostate cancer cell proliferation and phosphorylation of AKT and S6. (A and B) Exogenous RNASE4 (1 μg/ml) stimulates cell proliferation (A) and cell cycle progression (B) of DU145 cells cultured in the presence of 2% FBS. Cell numbers were determined by MTT assay. Cell cycle status was determined by flow cytometry after 24 hour incubation with RNASE4. (C) Time course of AKT and S6 phosphorylation of serum-starved DU145 cells by RNASE4 (1 μg/ml). Left panels, immunoblots; right panels, quantification of p-AKT and p-S6 normalized to total AKT and S6 by Image J analysis. (D) Effect of AKT inhibitor MK-2206, PI3K inhibitors Wortmannin and LY294002, and mTOR inhibitor Rapamycin on RNASE4-induced phosphorylation of AKT and S6. Cells were pre-incubated with the inhibitors at the indicated concentrations for 1 hour prior to be stimulated by 1 μg/ml of RNASE4 for 5 minutes. Top panels, immunoblots; bottom panels, Image J quantification of p-AKT and p-S6 normalized to total AKT and S6. (E) Effect of AKT inhibitor MK-2206, PI3K inhibitors Wortmannin and LY294002, and mTOR inhibitor Rapamycin on RNASE4-induced cell proliferation. DU145 cells were serum-starved overnight, incubated with the inhibitors for 1 hour, and then treated with RNASE4 (1 μg/ml) for three days. Cell numbers were determined by MTT assay. Data shown are from a representative experiments in triplicates of 3 independent repeats. Error bars indicate SEM. **$P \leq 0.01$, by unpaired two-tailed Student's t test.

FIGS. 12A-F. RNASE4 induces AXL phosphorylation. (A) Human phospho-receptor tyrosine kinase (RTK) antibody array analysis. Serum-starved DU145 cells were treated with or without 1 μg/ml of RNASE4 for 5 minutes. A total of 1.5 mg cell lysate protein was blotted on each array membrane. The right panel shows the mean pixel intensity of p-AXL. (B) Immunoblot analysis of RNASE4-stimulated AXL phosphorylation. DU145 cells were serum-starved overnight and treated with 1 μg/ml of RNASE4 for the indicated time. Cell lysates were analyzed by antibodies against total AXL and phospho-AXL, with β-actin as the loading control. Left panels, immunoblots; right panel, Image J quantification of p-AXL normalized to total AXL. (C) Immunoblot analysis of phospho-AXL in response to stimulation by ANG, RNase A, and RNASE4. DU145 cells were serum-starved overnight and treated with 1 μg/ml of ANG, RNase A, or RNASE4 for 15 minutes. Left panels, immunoblots; right panel, quantification. (D) Effect of AXL inhibitor R428 on RNASE4-induced cell proliferation. Serum-starved DU145 cells were incubated with 1 or 3 μM R428 for 3 hours and then stimulated by 1 μg/ml of RNASE4 for 3 days. Cell numbers were determined by MTT assay. Data shown are means±SEM of a representative experiment (in triplicates) of 3 independent repeats. $P \leq 0.01$ and *$P \leq 0.001$, by unpaired two-tailed Student's t test. (E) Effect of AXL inhibitor R428 on RNASE4-induced AKT and P6 phosphorylation. Serum-starved DU145 cells were incubated with 1 or 3 μM R428 for 3 hours and then stimulated by 1 μg/ml of RNASE4 for 5 minutes. Cell lysates were analyzed for AKT and P6 phosphorylation by immunoblotting. Top panels, immunoblots; bottom panels, quantification of phospho-AKT and phospho-S6 by Image J analyses normalized to total AKT and P6, respectively. (F) Schematic presentation of proposed involvement of AXL in RNASE4-stimulated cellular events.

FIGS. 13A-D. RNASE4 knockdown reduces prostate cancer cell proliferation in vitro and colony formation in soft agar. (A) Immunoblot analysis of RNASE4 in PC-3 cells stably transfected with shControl, shRNASE4-1, and shRNASE4-2. (B) qRT-PCR analysis of RNASE4 mRNA normalized to GAPDH in PC-3 cells stably transfected with shControl, shRNASE4-1, and shRNASE4-2. (C) Effect of RNASE4 knockdown on cell proliferation. Cell numbers were counted by a Coulter counter. Exogenous RNASE4, when presented, was at the concentration of 1 μg/ml. Data shown are from representative experiment (in triplicates) of 3 independent repeats. (D) Effects of RNASE4 knockdown on colonies formation and growth of PC-3 cells in soft agar. The same numbers of control and RNASE4 knockdown cells were seeded in soft agar, and grown in the absence or presence of 1 µg/ml of RNASE4 for 14 days. Colonies were counted and size measured on a Nikon Eclipse ti microscope. Left panels, representative images of colonies; scale bars=100 µm. Right panels, quantification of colony numbers and sizes. Data shown are means±SEM from five randomly selected fields per dish from a representative experiment. *P≤0.05, P≤0.01, and *P≤0.001, by two-tailed Student's t test.

FIGS. 14A-D. RNASE4 knockdown inhibits DU145 cell proliferation in vitro and colony formation in soft agar. (A) Immunoblot analysis of RNASE4 in DU145 cells stably transfected with shControl, shRNASE4-1, and shRNASE4-2. (B) qRT-PCR analysis of RNASE4 mRNA normalized to GAPDH in DU145 cells stably transfected with shControl, shRNASE4-1, and shRNASE4-2. (C) Effect of RNASE4 knockdown on cell proliferation. Cell numbers were counted by Coulter counter. Exogenous RNASE4, when presented, was at the concentration of 1 µg/ml. Data shown are from a representative experiment in triplicates of 3 independent experiments. (D) Effects of RNASE4 knockdown on colonies formation and growth of DU145 cells in soft agar. The same numbers of control and RNASE4 knockdown cells were seeded in soft agar, and grown in the absence or presence of 1 µg/ml of RNASE4 for 14 days. Colonies were counted and size measured on a Nikon Eclipse ti microscope. Top panels, representative images of colonies; scale bars=100 µm. Bottom panels, quantification of DU145 cell colonies and sizes in soft agar. Data shown are means±SEM of five randomly selected fields per dish from a representative experiment. P≤0.01 and *P≤0.001, by two-tailed Student's t test.

FIGS. 15A-D. RNASE4 knockdown inhibits LNCaP cell proliferation in vitro and colony formation in soft agar. (A) Immunoblot analysis of RNASE4 in LNCaP cells stably transfected with shControl, shRNASE4-1, and shRNASE4-2. (B) qRT-PCR analysis of RNASE4 mRNA normalized to GAPDH in LNCaP cells stably transfected with shControl, shRNASE4-1, and shRNASE4-2. (C) Effect of RNASE4 knockdown on LNCaP cell proliferation. Cell numbers were counted by Coulter counter. Exogenous RNASE4, when presented, was at the concentration of 1 µg/ml. Data shown are from a representative experiment in triplicates of 3 independent experiments. (D) Effects of RNASE4 knockdown on colonies formation and growth of LNCaP cells in soft agar. The same numbers of control and RNASE4 knockdown cells were seeded in soft agar, and grown in the absence or presence of 1 µg/ml of RNASE4 for 14 days. Colonies were counted and size measured on a Nikon Eclipse ti microscope. Top panels, representative images of colonies; scale bars=100 µm. Bottom panels, quantification of LMCaP cell colonies and sizes in soft agar. Data shown are means±SEM of five randomly selected fields per dish from a representative experiment. P≤0.01 and *P≤0.001, by two-tailed Student's t test.

FIGS. 17A-C. RNASE4 mAb inhibits prostate cancer cell proliferation and RNASE4-induced angiogenesis. (A) Effect of RNASE4 mAb on cell proliferation. DU145, PC-3, and LNCaP cells were cultured in the presence of 2% FBS. RNASE4 mAb or isotype control IgG2bκ were added at the concentrations indicated. Cell numbers were determined by a Coulter counter. (B) Effect of RNASE4 mAb on cell cycle distribution of DU145 cells. Cells were cultured in the 2% FBS and RNASE4 mAb (30 µg/ml) or isotype control IgG2bκ (30 µg/ml) for 3 days. Cell cycle status was determined by flow cytometry. (C) Effect of RNASE4 mAb on endothelail cell tube formation. HUVEC were cultured on Matrigel-coated wells and incubated in the absence or presence of 1 µg/m of RNASE4 with 30 µg/ml of RNASE4 mAb or isotype control IgG2bκ for 4 hours. Top panels, images of endothelial cell tubular structure of a representative experiment in duplicate of 3 independent repeats. Scale bar=50 µm. Bottom panels, tube length and number of loops counted from 5 randomly selected areas. Data shown are means±SEM. *P≤0.05, P≤0.01 and *P≤0.001, by two-tailed Student's t test.

FIG. 18. RNASE4 mAb does not inhibit basic FGF (bFGF)-induced angiogenesis. HUVEC were cultured on Matrigel-coated wells in basal endothelail cell culture medium and incubated in the absence or presence of 5 ng/ml of bFGF with 30 µg/ml of RNASE4 mAb or isotype control IgG2bκ for 4 hours. Untreated blank well was used as negative control. Top panels, images of endothelial cell tubular structure of a representative experiment in duplicate of 3 independent repeats. Scale bar=200 µm. Bottom panels, tube length and number of loops counted from 5 randomly selected areas. Data shown are means±SEM. ***P≤0.001 and ns=not significant, by two-tailed Student's t test.

FIG. 19. RNASE4 mAb inhibits RNASE4-mediated angiogenesis in a dose-dependent manner. HUVEC were cultured on Matrigel-coated wells in basal endothelial cell medium and stimulated with 1 µg/ml RNASE4 in the absence or presence of various concentrations of RNASE4 mAb or isotype control IgG2bκ for 4 hours. Untreated well was used as the negative control, and bFGF (5 ng/ml)-treated well was used as the postive control. Top panels, images of endothelial cell tubular structure of a representative experiment in duplicate of 3 independent repeats. Scale bar=200 µm. Bottom panels, tube length and number of loops counted from 5 randomly selected areas. Data shown are means±SEM. 0.05, P≤0.01, and *P≤0.001, by two-tailed Student's t test.

FIGS. 20A-E. RNASE4 mAb inhibits the establishment of xenograft human prostate cell tumors in athymic mice. PC-3 cells ($1 \times 10^6$ per mouse) were inoculated s.c. on the back of male athymic mice. One day post-inoculation, mice were treated by i.p. injection with PBS (n=6) or RNASE4 mAb (10 mg/kg, n=6) once every 3 days. (A) Tumor volume measured once every 3 days. (B) Animals were sacrificed on day 64, tumors were dissected and weighed. Left panel, tumor weight; right panel, representative images of tumors from PBS- and RANSE4 mAb-treated groups. (C) Body weight of PBS- and RNASE4 mAb-treated animals. (D) IHC analyses of Ki-67, CD31, total AXL, and phophoylated AXL (p-AXL) in tumor sections from PBS- and RNASE4 mAb-treated animals. Left panels, representative images; right panels, quantification of Ki-67 positive cells and CD31 positive neovessels from 5 randomly selected microscopic fields. (E) TUNEL staining of apoptotic cells. Nuclei were stained by DAPI. Right panels, representative images; right panel, percentage of TUNEL positive cells counted in five randomly selected areas. Data shown are means±SEM. Scale bars=100 µm. $P \leq 0.01$, *$P \leq 0.001$, and n.s.=not significant, by two-tailed Student's t test.

DETAILED DESCRIPTION

Figure 7A:
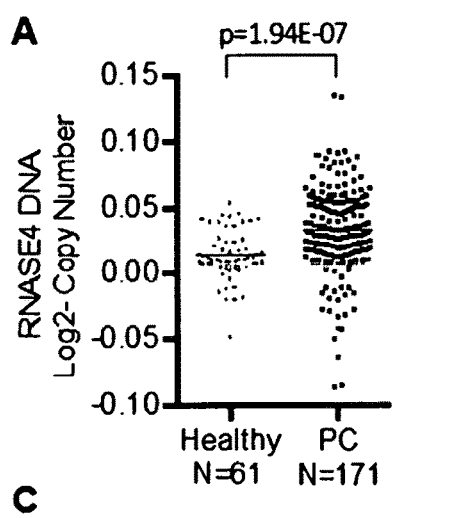
FIGS. 7A-D. Gain of RNASE4 and AXL gene copy numbers is associated with poor outcome of prostate cancer. (A and B) Bioinformatics data of RNASE4 (A) and AXL (B) DNA copy number variations from TCGA database (Oncomine.org) among healthy control subjects and prostate cancer (PC) patients. (C and D) Kaplan-Meier survival curves show the reverse correlation of the gain in gene copy number of RNASE4 (C) and AXL (D) with recurrence-free prostate cancer patient survival. Two-tailed Student's t test and log-rank (Mantel-Cox) test were used for statistical analysis.
Figure 7B:
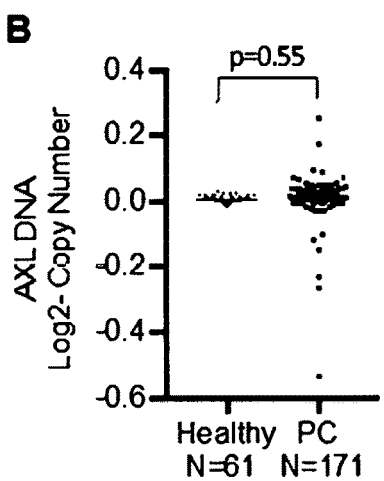
Figure 7C:
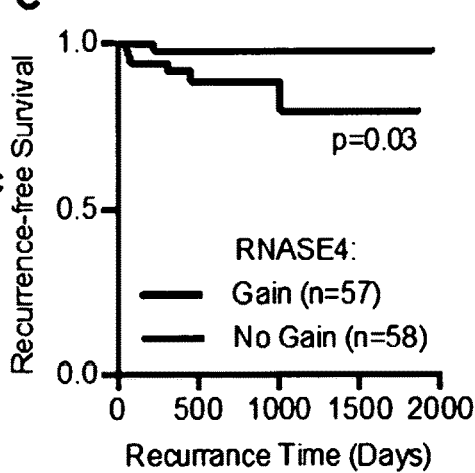
Figure 7D:
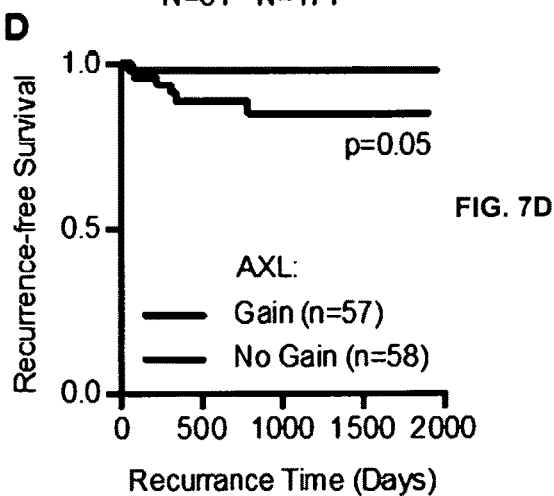

The invention provides methods and kits for use in diagnosing, preventing, and treating prostate cancer. The invention is based, at least in part, on our discovery that RNASE4 is up-regulated in prostate cancer, and thus has diagnostic, prognostic, and therapeutic applications. In particular, and as discussed further below, we have found that RNASE4 expression levels are increased progressively in prostate cancer, correlate with aggressiveness of the disease, and can accurately distinguish between healthy subjects and those with prostate cancer, as well as those with BPH and those with prostate cancer. Furthermore, we have found that RNASE4 levels can be used to independently predict biopsy outcome. We also have found that inhibition of RNASE4 decreases prostate cancer cell proliferation in vitro and in vivo, as well as RNASE4-induced angiogenesis, thus providing a basis for therapeutic methods. The methods and kits of the invention are described further below.

Diagnostic and Prognostic Methods

We have found that levels of RNASE4 are up-regulated in prostate cancer. For example, we found that RNASE4 protein levels in the plasma are elevated in prostate cancer patients and that its level is positively correlated with disease stage, grade, and Gleason score. Furthermore, we found that plasma RNASE4 levels can be used to predict biopsy outcome and to enhance accuracy of diagnosis, and that RNASE4 protein levels in prostate cancer tissues are enhanced and can differentiate prostate cancer and BPH. Accordingly, detection of RNASE4 levels can be used in diagnostic and prognostic methods (hereinafter collectively referred to as diagnostic methods), in a number of different contexts.

Most basically, detection of RNASE4 levels can be used to determine whether a subject, such as a human patient, has prostate cancer. In these methods, the levels of RNASE4 in a sample from the subject are determined and are compared to a reference level, which can be set by those of skill in the art. In one example, the reference level is an amount or range that is determined to be representative of that of subjects (e.g., age-matched subjects) that do not have prostate cancer, as determined, for example, by a particular type of assay (see, e.g., the assay types described below). Thus, for example, detection of an increased level of RNASE4 in a sample from a test subject, as compared to the level or range characteristic of healthy subjects, who do not have prostate cancer, can indicate that the test subject has prostate cancer. Alternatively, detection of a level of RNASE4 in a sample from a test subject that is within a normal range, or at or below a normal level, can indicate that the test subject does not have prostate cancer. In another example, the reference level is an amount or range that is representative of subjects that have prostate cancer. Detection of a lower RNASE4 level in a sample from a test subject, as compared to this reference level, can indicate that the test subject does not have prostate cancer, while detection of a higher or similar level can indicate that the test subject has prostate cancer. Optionally, multiple types of references (e.g., a normal/ healthy reference level or range, and/or a level or range characteristic of prostate cancer) can be used. In one example, detection of greater than 100 ng/ml (e.g., greater than 110, 120, 130, 140, or 150 ng/ml) in a plasma sample of a subject may be used to diagnose prostate cancer.

Detection of RNASE4 levels can also be used to distinguish between prostate cancer and benign prostate hyperplasia (BPH). This is particularly helpful because, for example, PSA is elevated not only in prostate cancer, but also in BPH and prostatitis. Thus, detection of elevated PSA levels can lead to unnecessary treatment and worry in patients who may not actually have prostate cancer. As RNASE4 levels differ between prostate cancer and BPH, the methods of the invention can be helpful in reducing false positives, and thereby reduce unnecessary treatment and patient worry. In these methods, a reference level used can be, for example, an amount or range that is determined to be representative of that of subjects (e.g., age-matched subjects) that have BPH. Thus, for example, detection of increased levels of RNASE4 in a sample from a test subject, as compared to the level or range characteristic of BPH, can indicate that the test subject has prostate cancer. Alternatively, detection of a level of RNASE4 that is within a range that is normal, or at or below a level associated with BPH, can indicate that the subject does not have prostate cancer. Rather, depending upon the RNASE4 level detected and, optionally, other features (e.g., clinical features), the subject may be determined to have BPH. Instead of, or in addition to, a BPH-associated reference level or range, a level or range characteristic of prostate cancer and/or normal/healthy subjects can be used.

We have observed that increased levels of RNASE4 are correlated with various clinical characteristics of prostate cancer including, for example, surgical T-stage, clinical stage, biopsy grade, and surgical Gleason scores. Higher levels of RNASE4 are also detected in subjects having distant or lymph node metastases. Accordingly, the methods of the invention can be used in an assessment of the prognosis of a subject, as well as in a determination of how advanced (or not) their prostate cancer may be. In particular, the level of RNASE4 in sample from a test subject can be determined and compared to a level or range characteristic of a particular clinical feature, prognosis, stage, grade, and/or level of risk of metastasis. A benefit of these methods is that they can be used to facilitate the selection of an appropriate approach to treatment for a subject based on specific features of their condition. This ensures that a subject will not be subjected to more severe treatment than needed, and also that a sufficient level of treatment is used under the circumstances of the patient's particular condition. The methods of the invention can similarly be used to determine the likelihood of metastasis or recurrence of prostate cancer in a patient. In a specific example, these methods can be used to distinguish aggressive vs. indolent tumors, an important distinction not discernable using PSA-based testing.

In more detail, RNASE4 levels can be correlated with a variety of different indicators of stage or grade of cancer. For example, correlations can be made with different aspects of the TNM staging system which, as is known in the art, includes the following stages and sub-stages: TX, T0, T1 (T1a, T1b, and T1c), T2 (T2a, T2b, and T2c), T3 (T3a, T3b, and T3c), T4, NX, N0, N1, MX, M0, and M1 (M1a, M1b, and M1c). Correlations can also be made with a histopathological Gleason score or group, such as a Gleason score of 6 or lower (well differentiated cells), Gleason 7 (moderately differentiated cells), Gleason 8-10 (poorly differentiated or undifferentiated cells), Gleason Group I (Gleason score 6), Gleason Group II (Gleason score 3+4=7), Gleason Group III (Gleason score 4+3=7), Gleason Group IV (Gleason score 8), and Gleason Group V (Gleason score 9 or 10); or risk category. With respect to risk categories, the test subject may be at very low risk (tumor not felt by DRE and not seen by imaging, but found by needle biopsy (T1c); PSA less than 10 ng/ml; Gleason score 6 or less; cancer found in fewer than 3 samples in core biopsy; cancer found in half or less of any core), low risk (tumor characterized as T1a, T1b, T1c, or T2a; PSA less than 10 ng/ml; Gleason score 6 or less), intermediate risk (tumor has two or more of the following characteristics: T2b or T2c; PSA between 10 and 20 ng/ml; Gleason score of 7), high risk (tumor has 2 or more of the following characteristics: T3a; PSA higher than 20 ng/ml; Gleason score between 8 and 10), or very high risk (T3b or T4; histologic grade of 5 for main pattern of cell growth or more than 4 biopsy cores with Gleason scores between 8 and 10). The RNASE4 levels can further be correlated with UCSF-CAPRA scores of 0 to 2 (low), 3 to 5 (intermediate), or 6 to 10 (high) risk of metastasis and death.

The methods of the invention can also be used to monitor a course of treatment. For example, if a subject is determined to have prostate cancer, e.g., using a method described herein, then the course of their treatment can be monitored to assess its progress. In these methods, RNASE4 levels can be determined, e.g., before, during, and/or after treatment. For example, if RNASE4 levels decrease over the course of treatment to levels and/or at a rate determined to be beneficial by those of skill in the art, then the treatment may be considered as being successful. Alternatively, if levels do not decrease or if they decrease in only a small amount or slowly, as compared to expectations for an effective outcome, then the treatment may be considered as not being successful. In such instances, it may be determined that it is best to proceed with a different course of treatment. The treatments that can be monitored according to these methods of the invention include, for example, treatment with an RNASE4 inhibitor (e.g., an antibody against RNASE4 or an RNASE4 binding fragment thereof; see below). The treatments also include, for example, radiation, surgery (e.g., prostatectomy or orchiectomy), cryotherapy, ultrasound therapy, hormone therapy (e.g., luteinizing-hormone releasing hormone (LHRH) agonists (e.g., leuprolide, goserelin, triptorelin, or histrelin) or LHRH antagonists (e.g., degarelix), anti-androgens (e.g., bicalutamide, flutamide, nilutamide, abiraterone, or enzalutamide), or combinations thereof), chemotherapy (e.g., docetaxel, optionally in combination with prednisone; mitoxantrone; or cabazitaxel), or immunotherapy (e.g., provenge).

The methods of the invention, involving detection of RNASE4 levels, can be carried out as the sole diagnostic method used. This provides substantial benefits with respect to features including efficiency and cost. Alternatively, the methods can be carried out in combination with other diagnostic methods. Thus, for example, the methods of the invention can be done in combination with the detection of one or more other biomarkers (e.g., PSA, a PSA derivative, ANG, and/or prostate cancer antigen 3), digital rectal examination, ultrasound, biopsy, MRI fusion, PET scanning, and genomic testing. However, the methods of the invention, in some instances, can be carried out so as to avoid the need for more invasive procedures such as, e.g., needle biopsy. In one example of particular combination methods of the invention, the performance of a PSA-based diagnostic test is enhanced by determination of both PSA and RNASE4 levels in a sample from a test subject. These methods are particularly beneficial in the context of subjects with low PSA levels (e.g., less than 4, 3, or 2 ng/ml), in which RNASE4 detection was found to be more accurate (see Examples, below). In view of these results, RNASE4 detection can advantageously be used for the diagnosis of earlier disease states in patients with low PSA (e.g., less than 2 ng/ml). In addition to standard PSA level analysis (e.g., PSA levels in a blood test), other PSA-related tests can be carried out in combination with RNASE4 detection methods including, e.g., analysis of percent free PSA, PSA velocity, and PSA density, as well as determination of a prostate health index (phi) or a 4Kscore test.

RNASE4 amounts can be determined at the level of, e.g., protein or mRNA using standard methods. Thus, for example, in the case of protein, levels can be determined using any of a number of known immunoassays and other approaches including, for example, enzyme-linked immunoassay (ELISA), immunohistochemistry (IHC), immunoprecipitation, Western blot, flow cytometry (e.g., fluorescence activated cell sorting), dot blot, radioimmunoassay, spectroscopy (e.g., mass spectroscopy), chromatography (e.g., HPLC), tumor microarray, and proteomics analysis. In the case of mRNA, methods including, e.g., RT-PCR, RT-qPCR, RNA-Seq, in situ hybridization, Northern analysis, microarray analysis, RNase protection, gene expression profiling, and multiplexed forms of any of these assays can be used. The assays listed here are exemplary only, as any of a wide variety of well-known assays can be used to assess expression, as is known in the art. Selection of a particular assay may be influenced by, e.g., the type of sample tested, available controls, and available testing equipment and facilities. Samples that can be tested using the methods of the invention include, for example, blood-based samples (e.g., whole blood, serum, and plasma samples), other biological fluids (e.g., urine), and tissue samples (e.g., prostate tissue biopsy samples, which may include prostate cancer cells). In specific examples, a tissue sample (e.g., a prostate biopsy) can be tested in order to distinguish BPH from prostate cancer.

Particular levels of RNASE4 expression that are diagnostic of prostate cancer (or a particular stage or feature thereof, or BPH) or characteristic of a reference, as described herein, can be determined by those of skill in the art. This can be done, e.g., by assessment of data or samples from normal/healthy subjects (e.g., pooled samples from unaffected individuals), or data or samples from patient populations (e.g., pooled samples from affected individuals). The patient populations can include, e.g., patients having a particular condition (e.g., prostate cancer or BPH) or a particular stage or grade of a particular condition (e.g., prostate cancer characterized by a certain stage or other clinical feature; see above).

The differences in levels of expression that are diagnostic of a particular condition can be determined by those of skill in the art. For example, standard methods can be used to determine the levels of RNASE4 that are to be set as diagnostic including, e.g., receiver operating characteristic (ROC) curve analysis (see, e.g., the Examples, below). In general, for example, a diagnostic difference in a level of expression can optionally be, e.g., an increase or decrease of about 1% or more (e.g., about 5% or more, 10% or more, about 20% or more, about 30% or more, about 40% or more, about 50% or more, about 60% or more, about 70% or more, about 80% or more, about 90% or more, about 100% or more, etc.), e.g., from about 1% to about 5%, from about 5% to about 10%, from about 10% to about 20%, from about 20% to about 30%, from about 30% to about 40%, from about 40% to about 50%, from about 50% to 60%, from about 60% to about 70%, from about 70% to about 80%, from about 80% to about 90%, from about 90% to about 100% or more, relative to a reference expression level.

In other instances, the level is increased or decreased by about 0.01-fold, 0.05-fold, 0.10-fold, 0.2-fold, 0.3-fold, 0.4-fold, 0.5-fold, about 0.6-fold, about 0.7-fold, about 0.8-fold, about 0.9-fold, about 1-fold, about 1.1-fold, about 1.2-fold, about 1.3-fold, about 1.4-fold, about 1.5-fold, about 1.6-fold, about 1.7-fold, about 1.8-fold, about 1.9-fold, about 2-fold, about 2.1-fold, about 2.2-fold, about 2.3-fold, about 2.4-fold, about 2.5-fold, about 3-fold, about 3.5-fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, or about 10-fold or greater, e.g., from about 0.01-fold to about 0.05 fold, from about 0.05-fold to about 0.10-fold, from about 0.10-fold to about 0.20-fold, from about 0.20-fold to about 0.4-fold, from about 0.5-fold to about 0.7-fold, from about 0.7-fold to about 1-fold, from about 1-fold to about 1.5-fold, from about 1.5-fold to about 2-fold, from about 2-fold to about 3-fold, from about 3-fold to about 4-fold, from about 4-fold to about 5-fold, from about 5-fold to about 6-fold, from about 6-fold to about 7-fold, from about 7-fold to about 8-fold, or from about 9-fold to about 10-fold or greater, relative to the reference expression level.

The subjects diagnosed according to the invention include human subjects, in particular male subjects, who have or are suspected of having prostate cancer. These subjects may have not received any treatment for prostate cancer, or may be in or have completed treatment. Furthermore, the subjects may be monitored according to the methods of the invention before, during, and/or after treatment, as noted above, in order to assess prognosis and determine the efficacy of treatment, as well as to determine likelihood of recurrence or metastasis.

Therapeutic Methods

In addition to discovering that RNASE4 levels are elevated in subjects with prostate cancer, we have also discovered that blocking or inhibiting RNASE4 inhibits proliferation of prostate cancer cells, as well as RNASE4-induced angiogenesis. Accordingly, the invention provides methods for treating, preventing, inhibiting, or reducing one or more symptoms of prostate cancer. The methods of the invention involve administering one or more RNASE4 inhibitors to a subject. The inhibitors can optionally act by blocking the activity of RNASE4. Thus, for example, an inhibitor such as an antibody can bind to RNASE4 and thereby inhibit RNASE4 activity. In other examples, the inhibitors can act by blocking expression of RNASE4 mRNA and/or protein.

Subjects that can be treated according to the methods of the invention include those that are diagnosed with prostate cancer using methods as described herein, as well as subjects who are diagnosed by other methods. The subjects can have, be at risk of developing, or be at risk of recurrence or metastasis of prostate cancer, of any stage or grade. Furthermore, the subjects may not have been treated previously for prostate cancer, may be concurrently be undergoing a different type of treatment for prostate cancer, or may have previously received a different type of prostate cancer.

In one example, the inhibitor is an antibody against RNASE4 or an RNASE4-binding fragment thereof. Thus, for example, the inhibitor can be a monoclonal antibody, a polyclonal antibody, a single chain antibody, a chimeric antibody, a human antibody, a humanized antibody, an antibody fragment (e.g., a Fab or a F(ab')2 fragment). Methods for the production of these and other types of antibodies are well known in the art. Other examples of inhibitors include other polypeptide-based agents, nucleic acid molecules (e.g., antisense and RNAi based approaches, with the latter using shRNA and siRNA molecules), small organic or inorganic molecules, and natural products or extracts.

Treatment according to the methods of the invention involves administration of one or more RNASE4 inhibitors, optionally in combination with other therapeutic agents or approaches (see below). Such treatment may result in, for example, reducing or delaying progression of prostate cancer (e.g., by a number of days, weeks, months, or years, e.g., by 2 months, 3 months, 4 months, 5 months, 6 months, 7 months, 8 months, 9 months, 10 months, 11 months, or 1 year or more), as compared to treatment that does not include the RNASE4 inhibitor. The treatment can also result in a lessening of symptoms, which may persist. Alternatively, the treatment can result in complete resolution of disease and symptoms.

RNASE4 inhibitors are formulated, dosed, and administered in manners determined to be appropriate by those of skill in the art. Factors considered in this context include the stage and/or grade of prostate cancer in the subject, the clinical condition of the subject, possible side-effects, the type of inhibitor, the mode of administration, the scheduling of administration, whether the RNASE4 inhibitor is administered for preventive or therapeutic purposes, previous therapy, the patient's clinical history and response to the RNASE4 inhibitor, and the discretion of the treating physician and other factors known in the art. As discussed below, the RNASE4 inhibitor can optionally be formulated with and/or administered concurrently with, one or more additional agents currently used to prevent or treat prostate cancer.

The duration of therapy can be for as long as medically indicated or until a desired therapeutic effect (e.g., those described herein) is achieved. Thus, for example, the therapy can optionally be carried out on a daily, weekly, bi-weekly, monthly, bi-monthly, or annual basis for 1 day, 1 week, 2 weeks, 1 month, 2 months, 4 months, 6 months, 8 months, 10 months, 1 year, 2 years, 3 years, 4 years, 5 years, or for a period of years up to the lifetime of the subject, or for a length of time falling within a range between these time points. The progress of therapy can be monitored by, e.g., a method described herein.

Inhibitors can be administered to subjects, such as human subjects, using standard methods that are selected based on the nature of the inhibitor. For example, administration can be systemic (e.g., oral, intravenous, or subcutaneous) or local (e.g., by injection, intralesional application, or topical application). Antibodies, for example, are typically administered intravenously.

The therapeutic methods of the invention can further involve administering to a subject an effective amount of an RNASE4 inhibitor (e.g., an antibody or antigen-binding fragment thereof) in combination with one or more additional therapeutic agents, and/or in conjunction with one or more additional approaches to treatment. The additional therapeutic agent(s) can be a second or further RNASE4 inhibitor or a different agent for use in the treatment of prostate cancer. Thus, for example, the additional therapeutic agent can be based on hormone therapy (e.g., luteinizing-hormone releasing hormone (LHRH) agonists (e.g., leuprolide, goserelin, triptorelin, or histrelin) or LHRH antagonists (e.g., degarelix), anti-androgens (e.g., bicalutamide, flutamide, nilutamide, abiraterone, or enzalutamide), or combinations thereof); chemotherapy (e.g., docetaxel); or immunotherapy (e.g., provenge). The additional approaches to treatment can also include, for example, any one or more of radiation (e.g., external-beam radiation therapy, intensity-modulated radiation therapy, proton therapy, or brachytherapy), surgery (e.g., prostatectomy (radical, robotic, or laparoscopic) or orchiectomy), focal therapy (e.g., cryotherapy), or ultrasound therapy. The additional therapeutic agents and/or approaches can be used in treatment regimens in combination with one or more RNASE4 inhibitor(s) in a manner determined to be appropriate by those of skill in the art. Thus, for example, the therapeutic agents can be administered in combination, either sequentially or concomitantly. Moreover, treatment combinations of one or more RNASE4 inhibitors, or combinations of RNASE4 inhibitors with other agents or approaches, can beneficially result in additive or synergistic therapeutic benefit to the patient.

Diagnostic Kits and Compositions

The invention provides diagnostic kits and compositions that include one or more reagents (e.g., polypeptides (such as antibodies or antigen-binding fragments thereof) or polynucleotides (e.g., probes or primers)) for determining the expression level of RNASE4 and, optionally, other biomarkers (e.g., PSA, PSA derivatives, ANG and/or prostate cancer antigen 3) in a sample from a test subject (e.g., a human subject suspected or at risk of having prostate cancer). The kits can optionally include one or more controls or reference samples that can be assayed and compared to a test sample, as described herein. Also, the kits can optionally include materials required for labeling and/or detecting reagents used in the methods. Furthermore, the kits can optionally include vessels, substrates, and/or other materials or tools for carrying out the methods of the invention (e.g., containers, vials, tubes, buffers, diluents, and labels). Each component of the kit can optionally be enclosed within an individual container and all of the various containers can optionally be within a single package, optionally together with instructions.

The instructions that are optionally included in the kits of the invention can, e.g., provide information as to how to use the kits to diagnose a subject with prostate cancer by, e.g., any of the methods described herein. In other examples, the kit may further include instructions to use the kit to select an appropriate course of treatment for a subject, or to evaluate the course of treatment. Furthermore, the instructions may provide information as to how to prepare samples for use in the methods, and/or information as to how to interpret results.

Examples

The invention is based in part on the experimental results described below. These examples are not to be construed as limiting of the invention in any way.

Results

Plasma RNASE4 Level is Elevated in Prostate Cancer Patients

RNASE4 level in the plasma samples of healthy control subjects (n=120) and prostate cancer patients (n=120) were determined by an in-house prepared ELISA. The demographics and clinical characteristics of the study population are shown in Table 1. There was no significant relationship between RNASE4 amount and patient demographics, such as age and race (Table 2). The intra- and inter-assay precision of the in-house ELISA were shown to be 95.1-98.2% and 90.7-94.1%, respectively (Table 3). The specificity and sensitivity of both polyclonal antibodies (pAb) and mAb of RNASE4, as well as a representative ELISA standard curve, are shown in FIG. 1. The recovery of RNASE4 spiked to levels throughout the range of the assay in plasma matric was also evaluated and shown to have a recovery range of 113-126% (Table 4). The median RNASE4 amount in plasma of prostate cancer patients (155.4±2.8 ng/ml) were significantly higher (P<0.0001) than in healthy control subjects (101.5±1.9 ng/ml) (FIG. 2A). The predictive value of RNASE4 was explored using receiver operating characteristic (ROC) curve analysis (FIG. 2B), which shows an AUC of 0.94 (0.91-0.97) at 95% CI. The diagnostic accuracy of RNASE4 differed depending on the cut-off values applied (Table 5). At the optimal cut-off value of 117 ng/ml, RNASE4 has a diagnostic accuracy of 86%, sensitivity of 94%, specificity of 80%, positive predictive value (+PV) of 83%, negative predictive value (−PV) of 93%, positive likelihood ratio (+LR) of 4.71 and negative likelihood ratio (−LR) of 0.07 (FIG. 2B, and Table 5).

In this cohort, PSA level in the plasma was also higher in prostate cancer patients (5.4±0.2 ng/ml) compared to control subjects (1.0±0.1 ng/ml) (P<0.0001) and showed an AUC of 0.98 (0.96-1.00) and a diagnostic accuracy of 93% (FIG. 3, A and B). At a cut-off value of 2 ng/ml, PSA sensitivity was 95% and specificity was 99%. PSA amount showed a significant positive correlation with age, but not race in control subjects, however had no correlation with age or race in prostate cancer patients (Table 6).

RNASE4 Enhanced the Performance of PSA in Prostate Cancer Diagnosis

ROC curve analysis of RNASE4 plus PSA showed an excellent diagnostic performance with an AUC of 0.99 (0.98-1.00) (FIG. 3C), suggesting that combining RNASE4 with PSA may give the most accurate diagnosis of prostate cancer. Further, ROC curve analysis showed that RNASE4 and PSA have an AUC of 0.72 and 0.64, respectively, in patient group with PSA values 2 ng/ml, and an AUC of 0.91 and 0.94, respectively, in patients with a PSA values 4 ng/ml (FIG. 3, D and E). A PSA value of 4 ng/ml and above is considered suspicious for the presence of prostate cancer, but for patients with PSA results below 2 ng/ml, there are currently no available biomarkers. These results suggest that RNASE4 performs better than PSA at predicting earlier disease states in patients with PSA levels less than 2 ng/ml.

Angiogenin (ANG), also known as ribonuclease 5 (RNASE5), is another member of the pancreatic ribonuclease superfamily and has been shown to promote prostate cancer progression (Dyer et al., Nucl. Acids Res. 33(3): 1077-1086, 2005; Sheng et al., Cancer Res. 74(19):1401-1041, 2014; Li et al., Mol. Cancer Res. 11(10):1203-1214, 2013; Katona et al., Clin. Cancer Res. 11(23):8358-8363, 2005; Yoshioka et al., Proc. Natl. Acad. Sci. U.S.A. 103 (39):14519-14524, 2006; Ibaragi et al., Clin. Cancer Res. 15(6):1981-1988, 2009) and to be co-regulated and co-expressed with RNASE4 (Olson et al., Clin. Cancer Res. 7(11):3598-3605, 2001; Yamasaki et al., J. Cell. Biol. 185 (1):35-42, 2009). We therefore also measured ANG levels in the plasma of this cohort of patients and found that plasma ANG amount was 475.1±8.6 ng/ml in prostate cancer patients, significantly higher than that in control subjects (379.3±6.3 ng/ml, P<0.0001) (FIG. 4A). These results are in agreement with previous reports that ANG improves diagnostic performance in prostate cancer screening (Pina et al., Eur. J. Cancer Prev. 23(3):166-172, 2014). As in case of RNASE4, ANG levels are not correlated to patient demographics (Table 7). ROC curve analysis of ANG showed an AUC of 0.79 at the 394 ng/ml optimal cut-off value (FIG. 4B), confirming that it is a good diagnosis marker for prostate cancer, but RNASE4 was significantly better with a higher AUC value (0.94). Not surprisingly, we found that ANG and RNASE4 were positively correlated (Pearson r=0.48, P<0.0001) (FIG. 4C) as they are known to share the same promoters and are co-expressed (Sheng et al., J. Biol. Chem. 289 (18):12520-12534, 2014). These data demonstrate that RNASE4 is a superior marker to ANG in prostate cancer diagnosis. Importantly, when RNASE4 is combined with PSA, a more accurate prediction can be made.

Tissue RNASE4 Level Distinguishes Prostate Cancer from BPH

Immunoblot (FIG. 2C) and qRT-PCR (FIG. 2D) analyses showed that RNASE4 expression is higher in prostate cancer cell lines PC-3, DU145, and LNCaP than in normal prostate epithelial cell line RWPE-1. Semi-quantitative analyses (FIG. 5) of IHC staining of RNASE4 in a tumor microarray (TMA) showed that the average RNASE4 IHC score in prostate cancer (n=50), BPH (n=20), and normal prostate (n=10) tissues was 2.9±0.1, 1.95±0.2, and 1.7±0.2, respectively (FIG. 2E). Thus, RNASE4 level in prostate cancer tissues was significantly higher than in BPH (P=0.0006) and normal prostate tissue (P=0.0005). Importantly, there was no significant differences between normal prostate and BPH samples (P=0.3861). These results suggest that RNASE4 can distinguish prostate cancer from BPH, a task PSA fails to accomplish (Chang et al., Nat. Rev. Clin. Oncol. 11(6): 308-323, 2014).

In silico analysis of RNASE4 mRNA utilizing Oncomine human multi-cancer datasets also revealed a significant up-regulation of RNASE4 mRNA in various types of human cancers, with the highest up-regulation observed in prostate cancer (FIG. 6). In The Cancer Genome Atlas (TOGA) prostate dataset, RNASE4 DNA copy number was also significantly higher ($P=1.94\times10^{-07}$) in prostate cancer tissues (n=61) than in healthy tissues (n=171) (FIG. 7A). Kaplan-Meier analysis showed that RNASE4 gene copy number is inversely correlated (n=57, log-rank test P=0.03) with recurrence-free survival. In silico analysis also showed that prostate gland has the second highest (next to urethra) RNASE4 mRNA level among various healthy organs (FIG. 8, A and B). These data show that RNASE4 is highly expressed in the prostate gland and differentially enhanced in prostate cancer but not in BPH.

RNASE4 Predicts Prostate Biopsy Outcome and is Correlated with Poor Prognosis

Figure 9A:
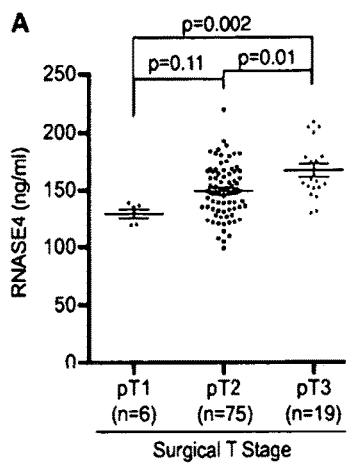
FIGS. 9A-I. RNASE4 protein levels in the plasma tissues of prostate cancer patients are correlated with poor prognosis and high risk of metastasis. (A-D) Correlation of plasma RNASE4 protein levels with tumor surgical T-stage (A), clinical stage (B), biopsy grade (C), and surgical Gleason (D). RNASE4 levels in the plasma were determined by ELISA. (E-I). Correlation of tissue RNASE4 levels with tumor histological grade (E), Gleason score (F), tumor stage (G), distant metastasis (H), and lymph node metastasis (I). Tissue RNASE4 levels were determined by semi-quantitative IHC. Each dot represents an individual sample. Lines represent the median values and the interquartile ranges. Statistical analyses were done by one-way ANOVA (A and B) and two-tailed Student's t test (C-I).
Figure 9B:
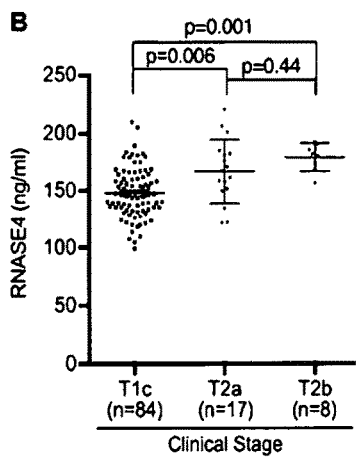
Figure 9C:
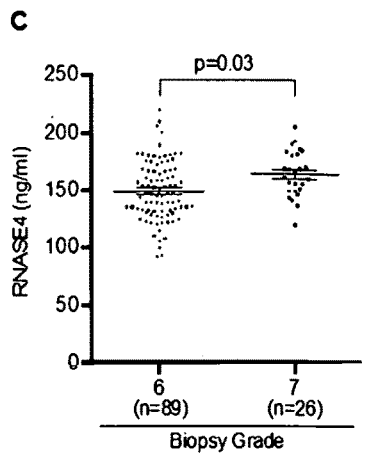
Figure 9D:
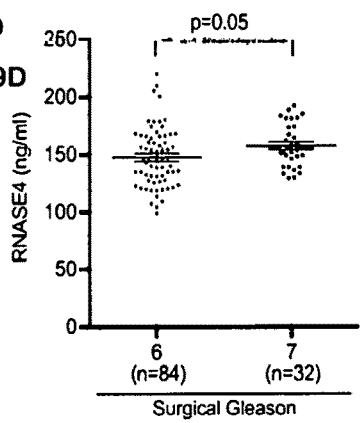
Figure 9E:
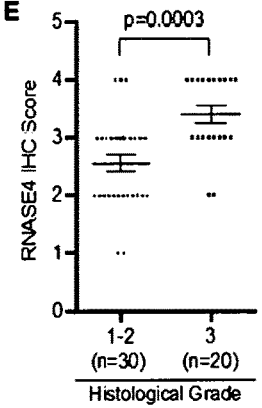
Figure 9F:
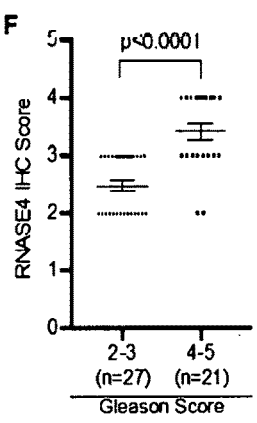
Figure 9G:
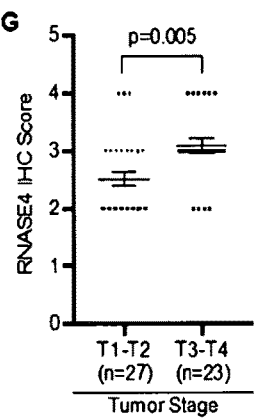
Figure 9H:
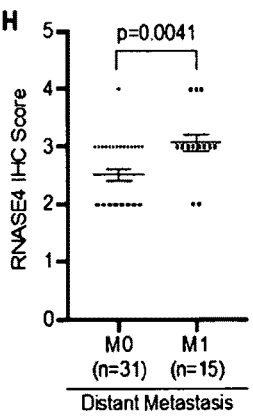
Figure 9I:
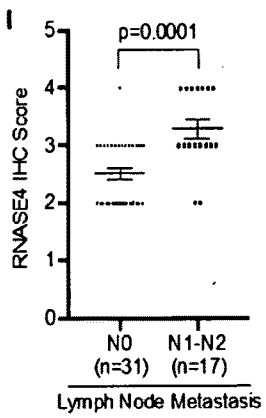

To explore the prognostic value of RNASE4, we examined the correlation between RNASE4 expression and prostate cancer aggressiveness. For this purpose, we first compared levels of RNASE4 protein in the plasma of prostate cancer patients of various clinical characteristics (Table 8), and found that RNASE4 was positively correlated with surgical T-stage, clinical stage, biopsy grade, and surgical Gleason scores of prostate cancer patients (FIG. 9, A-D), indicating that RNASE4 is associated with clinical characteristics of poor prognosis and high risk of metastasis. For example, plasma RNASE4 level in patients having pT3 tumors that extend beyond the prostate capsule was 166.8±5.6 ng/ml (n=19), significantly higher than those having pT2 tumors that are confined in the prostate gland (n=75, 149.5±2.7 ng/ml, P=0.01) (FIG. 9A). Patients at T2 clinical T-stage, representing tumors that invade one-half or less of the prostate lobe (T2a, n=17, 166.6±6.7 ng/ml, P=0.006) or more than one-half of the lobe (T2b, n=8, 178.5±4.2 ng/ml, P=0.001), had significantly higher plasma RNASE4 level than those with smaller, impalpable T1 tumors (T1c, n=84, 148.0±2.4 ng/ml) (FIG. 9B). Plasma RNASE4 levels in patients with less differentiated cancer tissues, such as tumors with biopsy grade 7 (n=26, 164.1±3.9 ng/ml, P=0.03) or surgical Gleason 7 (n=32, 157.8±3.3 ng/ml, P=0.05), were significantly higher than in those with well differentiated cancer tissues, such as tumors with biopsy grade 6 (n=89, 149.0±2.8 ng/ml) or surgical Gleason 6 (n=84, 147.8±3.1 ng/ml) (FIG. 9, C and D). Importantly, PSA failed to correlate with aggressiveness of the tumors (FIG. 3, F-I). It is noteworthy that while plasma level of ANG was also correlated with surgical and clinical stages, it was not correlated with biopsy grade and surgical Gleason scores (FIG. 4D-G), indicating that ANG is associated with aggressiveness of the tumor but not with their differentiation stage. These data suggest that RNASE4 is superior to PSA and to ANG as a prognosis marker of prostate cancer.

Logistic regression algorithm was used to assess whether RNASE4 can be used alone and in combination with PSA to predict biopsy outcome. Both univariate and multivariate logistic regression analyses (Table 9) showed that RNASE4 and PSA were significantly associated with biopsy status, but only RNASE4 was significantly associated with surgical T-stage, clinical stage, biopsy grade, and surgical Gleason. These results indicate that RNASE4 level in the plasma of prostate cancer patients is significantly associated with advanced disease status, demonstrating the diagnostic and prognostic value of RNASE4 as an independent biomarker to predict cancer and to determine disease stage prior to biopsy.

IHC analysis of RNASE4 in prostate cancer TMA (FIG. 5) revealed that the tissue level of RNASE4 was also positively correlated with histopathological characteristics (Table 10) of prostate cancer patients. The average IHC score of RNASE4 was significantly higher in prostate cancer with clinical characteristics that likely indicate a poor outcome and high risk of metastasis (FIG. 9, E-I). For example, RNASE4 is significantly higher in poorly differentiated tumors of histological grade 3 than in well-moderately differentiated tumors of histological grade 1 and 2

(P=0.0003) (FIG. 9E), in tissues with poorly formed glands of Gleason score 4 and 5 than in predominantly well-formed glands of Gleason score 2 and 3 (P<0.0001) (FIG. 9F), in advanced invasive tumors of T3 and T4 stage than in less invasive tumors of T1 and T2 stage (P=0.005) (FIG. 9G), and in those with distant or lymph node metastasis than in those with no metastasis (P=0.0041 and 0.0001, respectively) (FIG. 9, H and I). These results strongly suggest that RNASE4 can predict prostate biopsy outcome, and is correlated with poor prognosis and patient survival, and may thus serve as a prognosis marker.

Figure 11A:
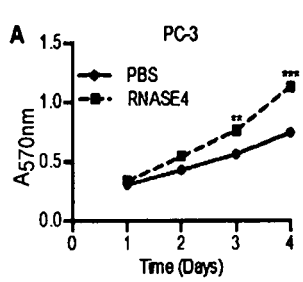
FIGS. 11A-F. RNASE4 induces PC-3 cell proliferation and phosphorylation of AKT and S6. (A) Exogenous RNASE4 (1 μg/ml) stimulates PC-3 cells proliferation in the presence of 2% FBS. Cell numbers were determined by MTT assay. (B) Time course of AKT and S6 phosphorylation of serum-starved PC-3 cells by RNASE4 (1 μg/ml). Left panels, immunoblots; right panels, quantification of p-AKT and p-S6 normalized to total AKT and S6 by Image J. (C) Effect of AKT inhibitor MK-2206, PI3K inhibitors LY294002 and Wortmannin, and mTOR inhibitor Rapamycin on RNASE4-induced PC-3 cell proliferation. Cells were pre-incubated with the inhibitors at the indicated concentrations for 1 hour prior to be stimulated by RNASE4 (1 μg/ml) for 3 days. Cell numbers were determined by MTT assay. (D) Human phospho-RTK antibody array analysis of starved PC-3 cells treated with or without 1 μg/ml RNASE4 for 5 minutes. (E) Time course of AXL phosphorylation stimulated by RNASE4 in PC-3 cells. Serum-starved PC-3 cells were treated with 1 μg/ml RNASE4 for different time. Cell lysates were analyzed for total AXL and phopho-AXL by immunoblotting. Left panels, immunoblots; right panel, quantification phospho-AXL normalized to total AXL by Image J analysis. (F) Effect of AXL inhibitor R428 on RNASE4-induced PC-3 cell proliferation. Serum-starved PC-3 cells were incubated with 1 or 3 μM R428 for 3 hours and then stimulated by 1 μg/ml of RNASE4 for 3 days. Cell numbers were determined by MTT assay. Data shown are means±SEM of a representative experiments in triplicates of 3 independent repeats. $P \leq 0.01$ and *$P \leq 0.001$, by unpaired two-tailed Student's t test.
Figure 11B:
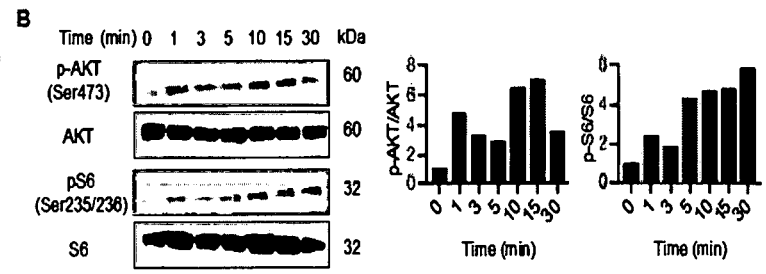
Figure 11C:
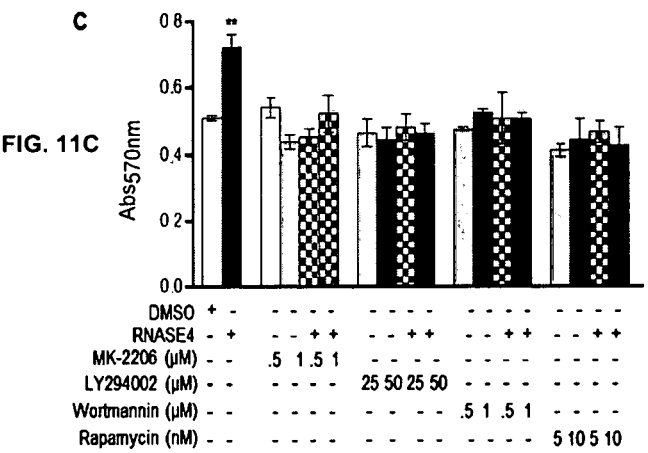

RNASE4 Induces Prostate Cancer Cell Proliferation by Activating PI3K-AKT-mTOR Pathway To investigate the functional role of RNASE4 in prostate cancer, we examined the effects of exogenous RNASE4 on prostate cancer cells, and found that RNASE4 stimulates proliferation of DU145 (FIG. 10A) and PC-3 cells (FIG. 11A). Cell cycle analysis of DU145 cells showed that a 3-day treatment with RNASE4 decreased G0/G1 population and increased G2/S/M phase population (FIG. 10B), consistent with enhanced proliferation in the presence of RNASE4. To investigate the mechanism of RNASE4-stimulated cell proliferation, we examined the effects of exogenous RNASE4 on the PI3K-AKT-mTOR pathway that has been known to play a key role in prostate cancer (Lee et al., J. Biol. Chem. 290(5):2759-2768, 2015), and found that AKT and S6 were rapidly and continuously activated by RNASE4 in DU145 (FIG. 10C) and PC-3 cells (FIG. 11B), which could be inhibited by AKT inhibitor MK-2206 and PI3K inhibitors LY294002 and Wortmannin (FIG. 10D and FIG. 11C). It is notable that Rapamycin, an mTOR inhibitor, inhibited S6 phosphorylation but not AKT phosphorylation. Consistently, RNASE4-induced cell proliferation was abolished by all these inhibitors (FIG. 10E and FIG. 11C). These data suggest that RNASE4 stimulates prostate cancer cell proliferation likely by activating the PI3K-AKT-mTOR signaling pathway.

RNASE4 Activates AXL to Stimulate Prostate Cancer Cell Proliferation

Figure 11D:
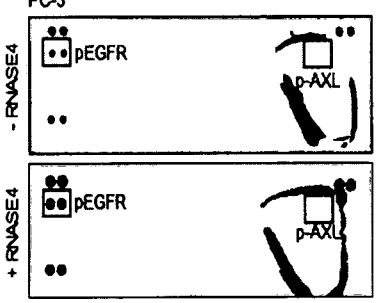
Figure 11E:
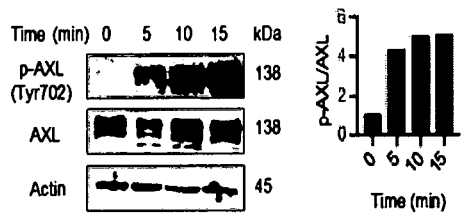

In order to know whether RNASE4-induced prostate cancer cell proliferation is mediated by a receptor tyrosine kinases, we performed human phospho-receptor tyrosine kinases (RTK) antibody array screening and found that RNASE4 treatment induced phosphorylation of AXL in DU145 (FIG. 12A) and PC-3 (FIG. 11D) cells. AXL is a mediator of cell growth and survival (Varnum et al., Nature 372(6515):623-626, 1995), and is up-regulated in several cancers (Zhang et al., Nat. Genet. 44(8):852-860, 2012; Gjerdrum et al., Proc. Natl. Acad. Sci. U.S.A. 107(3):1124-1129, 2010; Rankin et al., Cancer Res. 70(19):7570-7579, 2010), including prostate cancer (Paccez et al., Oncogene 32(6):689-698, 2013; Mishra et al., Mol. Cancer Res. 10(6): 703-712, 2012; Bansal et al., Oncotarget, 2015). RNASE4-induced AXL phosphorylation was confirmed by immunoblot analyses in DU145 (FIG. 12B) and PC-3 cells (FIG. 11E). Further, we found that the other members of the pancreatic ribonuclease superfamiy, including ANG and RNase A, do not induce AXL phosphorylation (FIG. 12C), suggesting that AXL is specifically activated by RNASE4.

Figure 11F:
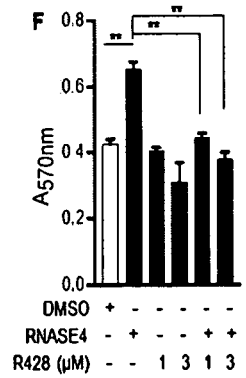

Next, we examined the effect of R428, a selective small molecule inhibitor of AXL kinase, on RNASE4-induced DU145 and PC-3 cell proliferation, and found that it inhibited RNASE4-induced cell proliferation (FIG. 12D and FIG. 11F) and AKT and S6 phosphorylation (FIG. 12E). These results suggest a plausible mechanism of action in which RNASE4 induces prostate cancer cell proliferation by activating AXL kinase and its downstream effectors AKT and S6 (FIG. 12F).

RNASE4 Knockdown Suppresses Prostate Cancer Cell Proliferation and Tumor Growth.

We next examined the cell-autonomous function of RNASE4 in prostate cancer proliferation by knocking down RNASE4 in PC-3 (FIG. 13, A and B), DU145 (FIG. 14, A and B), and LNCaP (FIG. 15, A and B) cells with two RNASE4-specific shRNAs (shRNASE4-1 and shRNASE4-2) with a non-targeting shRNA control (shControl). Knockdown of RNASE4 decreased prostate cancer cell proliferation (FIG. 12C, FIGS. 14C and 15C) and reduced both number and size of prostate cancer cell colonies in soft agar (FIG. 13D, FIGS. 14D and 15D). Importantly, exogenous RNASE4 was able to rescue the effect of RNASE4 knockdown in both cell proliferation (FIG. 13C, FIGS. 14C and 15C) and colony formation (FIG. 13D, FIGS. 14D and 15D) assays.

Figure 16A:
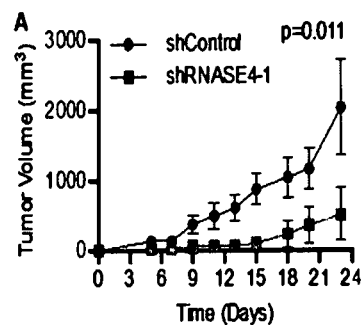
FIGS. 16A-D. RNASE4 knockdown slows down xenograft growth of human prostate cancer cell tumors in athymic mice. (A) Growth curve of PC-3 control and RNASE4 knockdown cells in athymic mice. Same number of shControl- and shRNASE4-1-tranfected PC3 cells ($1 \times 10^6$ per mouse) were inoculated s.c. on the right lower back of nude mice (n=6 per group). Tumor volume was measured two times per week. (B) Tumor weight derived from control and RNASE4 knockdown PC-3 cells. On day 24, mice were sacrificed, and their tumors were dissected and weighed. (C) IHC analyses of RNASE4, Ki-67, and CD31 in tumor sections derived from control and RNASE4 knockdown PC-3 cell. Quantification of Ki-67 positive cells and CD31 positive neovessels were from 5 randomly selected microscopic fields. Scale bars=100 µm. Data shown are means±SEM. (D) IHC analyses of total AXL and phosphoylated AXL (p-AXL) in tumor sections derived from control and RNASE4 knckdown PC-3 cell. Scale bars=100 µm. 0.05, P≤0.01 and *P≤0.001, by two-tailed Student's t test.
Figure 16B:
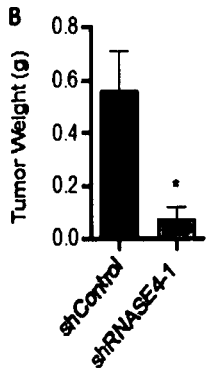
Figure 16C:
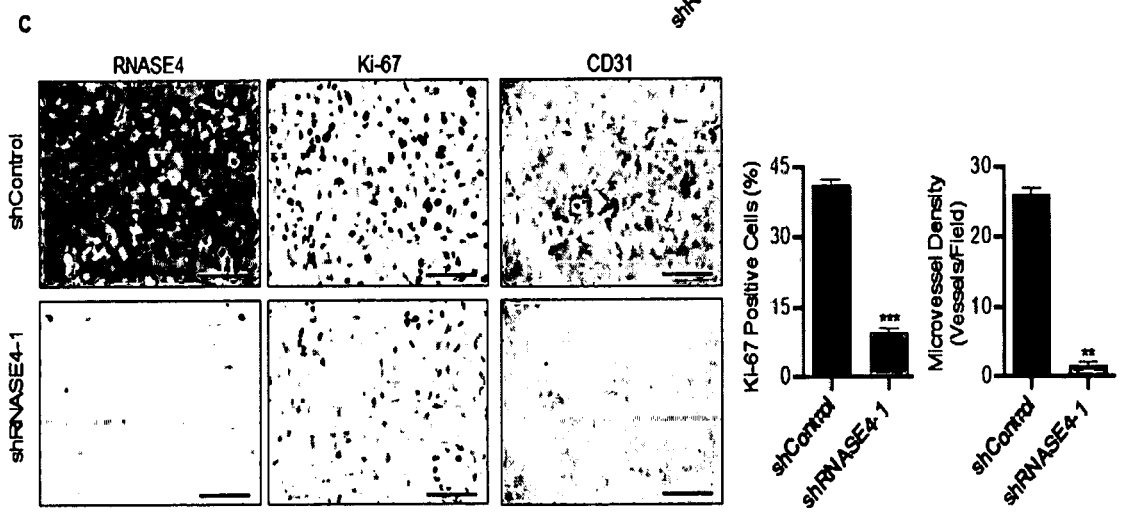
Figure 16D:
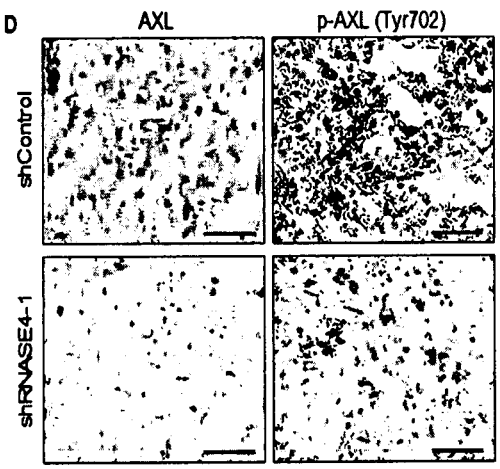

The effect of RNASE4 knockdown on tumor growth was examined in a xenograft animal model with PC-3 cells. Compared to mice injected with shControl-transfected cells, tumor growth was significantly slower in mice inoculated with shRNASE4-transfected cells as reflected by a 75±6% decrease in tumor volume (FIG. 16A, P=0.011) and 88±3% decrease in tumor weight on day 23 when animals were sacrificed and tumors dissected (FIG. 16B, P=0.03). IHC staining confirmed the reduction of RNASE4 protein in tumors derived from shRNASE4-transfected cells compared to those derived from shControl-transfected cells (FIG. 16C). The percentage of Ki-67 and CD31 positive cells were also decreased in RNASE4 knockdown tumors (FIG. 16C), indicating a decrease in cell proliferation and in tumor angiogenesis upon RNASE4 knockdown. Consistent with AXL being a mediator for RNASE4, we observed a decreased level of phosphorylated AXL in RNASE4 knockdown tumors while the level of total AXL was not significantly changed (FIG. 16D).

RNASE4 mAb Inhibits Prostate Cancer Cell Proliferation and RNASE4-Induced Angiogenesis.

To evaluate the therapeutic value of targeting RNASE4 in prostate cancer therapy, we generated human RNASE4-specific mAb (FIG. 1) and examined its effect on prostate cancer cell proliferation. As show in FIG. 17A, RNASE4 mAb inhibited proliferation of DU145, PC-3, and LNCaP cells in a dose-dependent manner. Consistently, it significantly decreased the population of cells in G2/S/M phase and correspondingly increased G0/G1 population (FIG. 17B). RNASE4 is known to be angiogenic (Li et al., Angiogenesis 16(2):387-404, 2013). We therefore examined the effect of RNASE4 mAb on RNASE4-induceded angiogenesis by in vitro endothelial cell tube formation assay, and found that it had no effect to bFGF-induced endothelial cell tube formation (FIG. 18), but inhibited RNASE4-induced endothelial cell tube formation (FIG. 17C) in a dose-dependent manner (FIG. 19). These results demonstrate the effectiveness and specificity of RNASE4 mAb in inhibiting RNASE4-mediated cell proliferation and angiogenesis.

RNASE4 mAb Suppresses Prostate Tumor Growth In Vivo

The anti-tumor activity of RNASE4 mAb was first examined in a prophylactic setting in a xenograft animal model in which PC-3 cells were inoculated into athymic mice and treatment was started the next day. Antibody was administrated by i.p. injection at 10 mg/kg once every 3 days for 63 days. As shown in FIGS. 20A and 20B, this treatment regimen resulted in a 90±3% inhibition in tumor weight (P=0.05) and a 80±5% inhibition tumor volume (P=0.0014).

Body weight of the animals was not changed (FIG. 20C) upon mAb treatment, suggesting no or low toxicity by inhibiting RNASE4. IHC analysis of Ki-67 and CD31 showed that cancer cell proliferation and tumor angiogenesis were significantly reduced (FIG. 20D), while TUNEL staining showed that apoptosis was enhanced upon mAb treatment (FIG. 20E). A reduction in phospho-AXL was also observed in RNASE4 mAb-treated tumors (FIG. 20D). These results indicate that RNASE4 mAb inhibited the establishment and growth of PC-3 xenograft tumors in athymic mice, accompanied by a reduction in tumor cell proliferation, tumor angiogenesis, and an increase in tumor cell apoptosis, as well as the involvement of AXL in these processes.

Figure 21A:
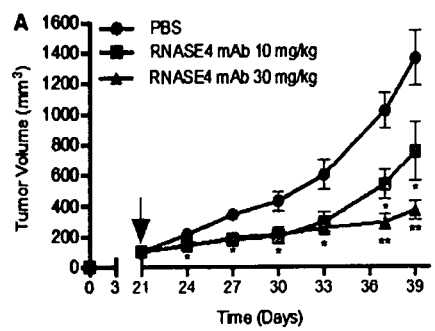
FIGS. 21A-D. RNASE4 mAb inhibits the growth of established xenograft human prostate cell tumors in athymic mice. PC-3 cells ($1 \times 10^6$) were inoculated s.c. on the back of male athymic mice. After tumors reached ~100 mm³ in volume (day 21), mice were grouped and treated by i.p. injection of PBS (n=12) or RNASE4 mAb (10 mg/kg or 30 mg/kg, n=6 per group) three times per week. (A) Tumor volume measured every 3 days. (B) Tumor weight. Mice were sacrificed on day 39, tumors were dissected and weighed. Left panel, average tumor weight; right panel, representative tumor images from the three groups. (C) IHC analyses for ki-67, CD31, total AXL, and phosphorylated AXL (p-AXL). Left panels, representative images; right panels, quantification of Ki-67 positive cells and CD31 positive neovessels from 5 randomly selected microscopic fields. (D) TUNEL staining of apoptotic cells. Nuclei were stained by DAPI. Right panels, representative images; right panel, percentage of TUNEL positive cells in five randomly selected areas. Data shown are means±SEM. Scale bars=100 µm. *$P \leq 0.05$ and **$P \leq 0.01$, by two-tailed Student's t test.
Figure 21B:
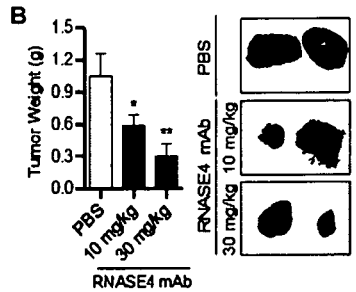
Figure 21C:
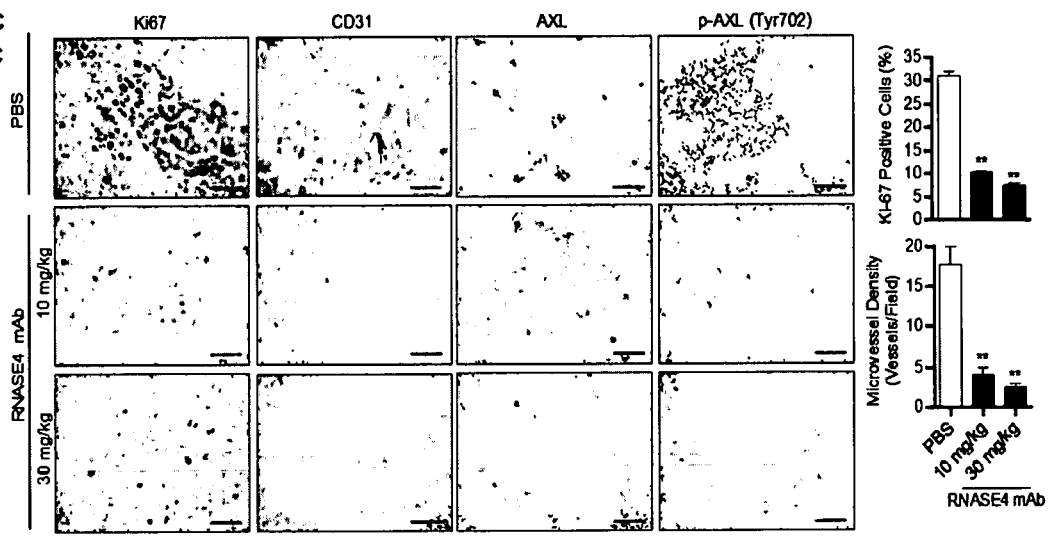
Figure 21D:
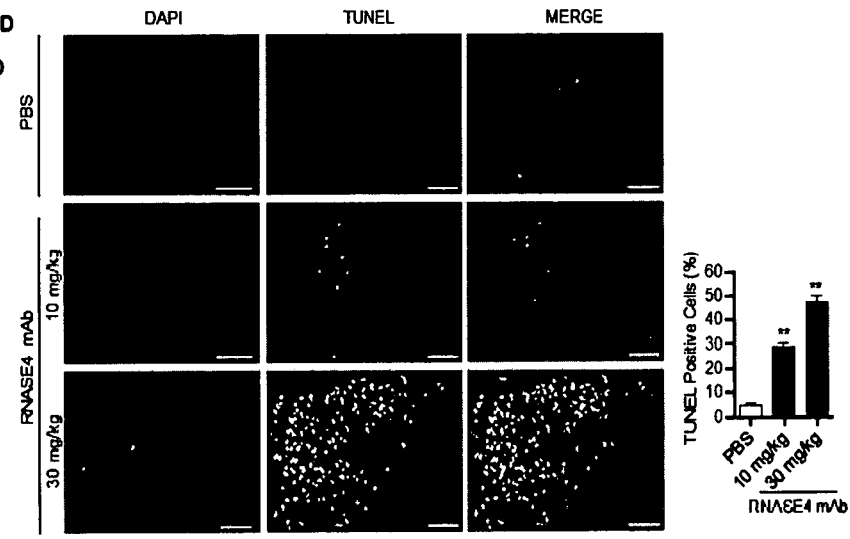

Next, we evaluated the effectiveness of RNASE4 mAb against already established tumors. PC-3 cells were inoculated into athymic mice and waited for 21 days until xenograft tumors reached a size of approximately 100 mm³. The tumor-bearing animals were separated into 3 groups according to tumor sizes so that each group had animals with matched tumor sizes, and treated with PBS (n=12) or with RNASE4 mAb at 10 mg/kg (n=6) and 30 mg/kg (n=6), respectively, by i.p. injection once every 3 days for 39 days. FIG. 21 shows that RNASE4 mAb dose-dependently inhibited growth of established PC-3 xenograft tumors in athymic mice. Treatment with 30 mg/kg resulted in a reduction of 72.7±6% in tumor volume (FIG. 21A) and 70.0±3% in tumor weight (FIG. 21B). Again, IHC analyses show that RNASE4 mAb-treated tumors displayed a reduced staining of Ki67, CD31, and phosphorylated AXL (FIG. 21O), and an increased TUNEL staining (FIG. 21D). Taken together, these results provide in vivo evidence that RNASE4 is a therapeutic target for the treatment of prostate cancers.

Methods

Human Plasma Samples

A total of 240 plasma samples (120 healthy, 120 prostate adenocarcinoma) were collected at Johns Hopkins University and obtained from Prostate Cancer Biorepository Network (PCBN), in compliance with institutional guidelines, as approved by the Institutional Review Board (IRB) of Tufts Medical Center/Tufts Medical School and Johns Hopkins University School of Medicine. Plasma samples were diluted 1:10 in PBS prior to performing RNASE4 ELISA.

Tumor Xenograft Experiments

Six- to eight-week-old male athymic nude (CrTac: NCr-Foxn1$^{nu}$ background) mice were obtained from Taconic Biosciences. Mice at age 7-8 weeks were injected s.c. in the right flank with 1×10⁶ viable cells in 100 µl HBSS. Six mice per group were used. Tumor size was monitored by digital caliper. Tumor volume was calculated by $V=(L \times W^2)/2$, where L is length at the widest point of the tumor and W is the maximum width perpendicular to L. For the prophylactic treatment of RNASE4 mAb, one day after PC-3 cell inoculation, mice were randomized into treatment groups, and administered with RNASE4 mAb (10 mg/kg) or PBS once every 3 days by i.p. injection. For the therapeutic treatment, mice were randomized into treatment groups once tumors reached ~100 mm³ and treated with i.p. injection of PBS or RNASE4 mAb at 10 or 30 mg/kg once every 3 days.

Recombinant Human RNASE4 Protein and RNASE4 Antibodies

Recombinant human RNASE4 protein was generated using a pET11 expression system in *E. coli* and purified by reversed-phase HPLC as previously described (Li et al., Angiogenesis 16(2):387-404, 2013). RNASE4 pAb were generated using RNASE4 recombinant protein as the antigen, and affinity purified using RNASE4-Sepharose column. RNASE4 mAbs were generated by immunizing BALB/c mice, followed by fusion with Sp2/0 mouse myeloma cells. The mAb used in this study was purified by Protein G affinity chromatography from hybridoma cell culture adapted to serum free conditions.

RNASE4 ELISA

ELISA plates were coated with 10 µg/ml RNASE4 mAb, 100 µl per well, in 100 mM sodium carbonate-bicarbonate buffer (pH 8.5) overnight at 4° C. After blocking with 5 mg/ml BSA in PBS (300 µl/well) for 1 hour at RT and four washes with PBST (10 mM phosphate buffer pH 7.4, 150 mM NaCl, 0.025% Tween-20), standards and samples were added (100 µl/well) and incubated overnight at RT. After four washes with PBST, 100 µl of 0.75 µg/ml of rabbit RNASE4 pAb was added to each well and incubated for 2 hour at RT. Following another four washes, alkaline phosphatase conjugated goat anti-rabbit antibody (1:1000) was added to the wells and incubated for 1 hour at RT. Following four washes, 100 µl of 0.5 mg/ml p-nitrophenyl phosphate in 10 mM diethanolamine, 0.5 mM $MgCl_2$, pH 9.5, was added to each well and incubated at RT for 1-4 hours, and absorbance at 450 nm was measured on a plate reader. The minimum detectable dose (MDD) of human RNASE4 is typically 0.5 ng/ml. The MDD was determined by adding two standard deviations to the mean optical density value of twelve zero standard replicates and calculating the corresponding concentration. No significant cross-reactivity was observed with ANG at 1 µg/ml. Cross-species reactivity was not observed with mouse RNASE4. Three samples of known concentration were tested twelve times on one plate to assess intra-assay precision. Three samples of known concentration were tested in twelve separate assays to assess inter-assay precision. Recovery of human RNASE4 spiked to levels throughout the range of the assay in human plasma was evaluated.

Prostate Tissue Array

A TMA containing 50 cases of prostate adenocarcinoma, 20 cases of BPH, and 10 cases of normal prostate tissue was purchased from US Biomax (PR807a). A core of malignant tissue marker, hepatocellular liver cancer, was included in the array. Each array spot was 1.5 mm in diameter and 5 µm in thickness. The histological diagnosis, grading using the Gleason scoring system, and TNM grading were supplied by the manufacturer for each array. Detailed information for the array can be viewed at www.biomax.us/tissue-arrays/Prostate/PR807a (prostate cancer, hyperplasia and normal tissue array).

Inhibitors

AXL inhibitor R428 was purchased from ApexBio. MK-2206 was from Selleckchem. Wortmannin was from Sigma. Rapamycin and LY294002 were purchased from Cell Signaling Technology.

RNA Extraction and qRT-PCR

Total cellular RNA was isolated using TRIzol reagent (Invitrogen) and reverse-transcribed (1 µg) to cDNA with random and oligo(dT)18 primers by M-MLV reverse transcriptase (Promega). For estimation of RNASE4 copy numbers, samples were reverse transcribed simultaneously with a standard series of cRNA samples ($10^9$-$10^3$ copies per reaction) and cDNAs amplified on a Light Cycler 480 II (Roche) using SYBER Green PCR mix (Roche). GAPDH was used as an internal control. The primers are RNASE4 forward: 5'-AGAAGCGGGTGAGAAACAA-3', reverse: 5'-AGTAGCGATCACTGCCACCT-3'; GAPDH forward: 5'-TGAACGGGAAGCTCACTGG-3', reverse: 5'-TCCAC-CACCCTGTTGCTGTA-3'.

Cell Cycle Analysis

For flow cytometry analyses, $1\times10^6$ cells were fixed and permeabilized using Cytofix/Cytoperm Fixation/Permeabilization Kit (BD). Cells were stained with Ki67 FITC (BD, 1:10 in BD Perm/Wash buffer), washed, and then stained with DAPI (2 µg/ml) for 10 minutes, directly prior to analysis. Cyan ADP LX7 Analyzer flow cytometer was used.

Bioinformatics

An in silico analysis on RNASE4 mRNA expression of Bittner Multi-cancer (n=1,911), Su Multi-cancer (n=174) and Roth Normal 2 (n=504) datasets in a public cancer microarray database Oncomine (www.oncomine.org) was performed. In Bittner Multi-cancer dataset, RNASE4 in cancer tissues were normalized to corresponding healthy tissues. In Roth Normal 2 dataset, RNASE4 in prostate tissue was compared to all other tissues to derive higher/lower RNASE4 expression in the specific normal tissue. All microarray datasets were scaled to zero by subtracting the median from each value. This step was performed by Oncomine to remove bias in signal intensity between samples. The Oncomine™ Platform (Thermo Fisher) was used for statistical analysis and visualization. Copy number gain of RNASE4 and AXL DNA and survival probability of patients with RNASE4 and AXL copy number variations were analyzed in (DNA) TOGA Prostate dataset (n=308) in Oncomine. RNASE4 and AXL copy numbers were analyzed in tissue specimens only, excluding blood specimens, in TCGA Prostate dataset (n=232).

Immunohistochemistry

Paraffin-embedded tissue sections were deparaffinized in xylene, followed by treatment with a graded series of alcohols (100%, 95%, 70%, and 50% ethanol) and rehydration in PBS (pH 7.5). For antigen retrieval, the sections were immersed in 10 mM Sodium Citrate, 0.05% Tween 20, pH 6.0, and heated in a microwave for 20 minutes. After washing in PBS, endogenous peroxidases were blocked with 0.3% hydroxyl peroxide in TBS for 15 minutes, followed by 2 washes in TBS. The sections were blocked with 10% goat serum with 1% BSA in TBS in a humidified chamber for 2 hours at RT and then incubated with the primary antibodies diluted in TBS with 1% BSA overnight at 4° C. For RNASE4 staining, 2 µg/ml of affinity purified human RNASE4 pAb was incubated for 3 hours at RT. HRP conjugates of goat anti-mouse or rabbit IgG were used as secondary antibodies. DAB was used for color development. Slides were counterstained with Modified Mayer's Hematoxylin.

RNASE4 Knockdown Cell Lines

Lentiviral mediated shRNA system (pGIPZ, Open Biosystems) was used to generate control and RNASE4 knockdown cell lines. The sequences were: shControl, 5'-ATCTCGCTTGGGCGAGAGTAAGTA-3', shRNASE4-1, 5'-ACCTGTCAGGGAGGCATT AAA-3'; shRNASE4-2, 5'-CAAAGAGATATGGAGACATAA-3'.

In Vitro Angiogenesis Assay

HUVEC, $1\times10^5$ cells in 50 µl endothelial cell basal medium (Invitrogen) were plated on a Matrigel (BD Biosciences) treated µ-slide (µ-slide angiogenesis, Ibidi) and incubated with 1 µg/ml RNASE4 and 30 µg/ml RNASE4 mAb or 30 µg/ml isotype control IgG. Tube formation was examined under microscope over a period of 4-5 hours. Image analysis to quantify number of loops and total tube length was performed by ImageJ software and WimTube image analysis tool.

Human Phospho-RTK Array

Human Phospho-RTK Arrays were purchased from R&D Systems. Cells were starved overnight and treated with 1 µg/ml RNASE4 for 5 minutes before sample collection. Protein concentrations were quantified by Bradford Assay and 1.5 mg cell lysate was used per array. Pixel densities on were analyzed by ImageJ. Average background signal from each array was subtracted using PBS negative control spots during data analysis.

Statistics

Data were presented as means±SEM. GraphPad Prism 7.0 (GraphPad Software) was used for statistical analysis. Comparisons between 2 groups were analyzed by 2-tailed Student's t test and comparisons of multiple groups by 1-way ANOVA, post hoc intergroup comparisons, and Tukey's test. Kaplan-Meier survival curves were analyzed using log-rank test. ROC curves were generated by MedCalc and Prism. Regression analyses were performed by MedCalc and Stata Softwares. The p values were indicated by stars as follows: $*p<0.05$, $p<0.01$, $*p<0.001$.

TABLE 1

Demographic and clinical characteristics of study population

| Characteristic | All subjects (N = 240)[A] | Healthy (n = 120)[A] | Prostate Cancer (n = 120)[A] |
|---|---|---|---|
| Age (years) | | | |
| Mean | 58.6 | 57.4 | 59.8 |
| Min-Max | 42-86 | 42-86 | 43-77 |
| Race | | | |
| White/Non-Hispanic n (%) | 215 (86) | 104 (86.6) | 111 (92.5) |
| African-American n (%) | 16 (6.6) | 9 (7.5) | 7 (5.8) |
| Asian n (%) | 3 (1.2) | 2 (1.6) | 1 (0.8) |
| Other n (%) | 5 (2) | 4 (3.3) | 1 (0.8) |
| PSA before biopsy (ng/ml) | | | |
| Mean | 2.13 | 0.96 | 5.42 |
| Min-Max | 0.2-19.4 | 0.2-2.4 | 0.3-19.4 |
| ≤2 n (%) | 116 (48.3) | 111 (92.5) | 5 (4.2) |
| ≤4 n (%) | 146 (60.8) | 118 (98.3) | 28 (23.3) |
| <10 n (%) | 226 (94.2) | 118 (98.3) | 108 (90) |
| ≥10 n (%) | 8 (3.3) | 0 (0) | 8 (3.3) |

[A]Patient numbers may not add to the total sample size due to item nonresponse.

TABLE 2

Plasma RNASE4 level is not correlated with patient demographics

| | RNASE4 (ng/ml) Mean ± SEM | | | |
|---|---|---|---|---|
| Clinical features | Healthy (n = 120)[A] | P-value | Prostate Cancer (n = 120)[A] | P-value |
| Age (years) | | | | |
| 40-49 | 104.7 ± 4.1 (n = 33) | | 144.4 ± 10.5 (n = 6) | |
| 50-59 | 100.6 ± 2.9 (n = 39) | p = 0.41 | 154.7 ± 3.2 (n = 62) | p = 0.34 |

TABLE 2-continued

Plasma RNASE4 level is not correlated with patient demographics

| Clinical features | RNASE4 (ng/ml) Mean ± SEM | | | |
|---|---|---|---|---|
| | Healthy (n = 120)[A] | P-value | Prostate Cancer (n = 120)[A] | P-value |
| 60-69 | 97.2 ± 3.9 (n = 34) | p = 0.19 | 153.2 ± 3.9 (n = 40) | p = 0.42 |
| 70-89 | 110.2 ± 4.7 (n = 13) | p = 0.46 | 137.2 ± 7.8 (n = 12) | p = 0.60 |
| Race/Ethnicity | | | | |
| White/Non-Hispanic | 102.3 ± 2.0 (n = 104) | | 128.0 ± 2.3 (n = 111) | |
| African-American | 94.4 ± 9.8 (n = 9) | p = 0.28 | 147.8 ± 9.3 (n = 7) | p = 0.13 |
| Asian | 95.0 ± 5.0 (n = 2) | p = 0.61 | 185.1 ± 0 (n = 1) | n/a |
| Caribbean/West Indiain/Hispanic | 84.7 ± 7.0 (n = 2) | p = 0.23 | 139.7 ± 0 (n = 1) | n/a |
| Other | 132.9 ± 18.6 (n = 2) | p = 0.04 | n/a | n/a |

[A]Patient numbers may not add to the total sample size due to item nonresponse.
n/a = information not available.
Statistical analysis was performed by unpaired, two-tailed Student's t test.

TABLE 3

Assay validation of RNASE4 ELISA Precision[A]

| | Intra-assay Precision | | | Inter-assay Precision | | |
|---|---|---|---|---|---|---|
| | Sample | | | | | |
| | 1 | 2 | 3 | 1 | 2 | 3 |
| n | 12 | 12 | 12 | 12 | 12 | 12 |
| Mean (ng/ml) | 1.05 | 2.1 | 4.21 | 1.05 | 2.1 | 4.21 |
| Standard deviation | 0.013 | 0.008 | 0.011 | 0.016 | 0.035 | 0.041 |
| CV (%) | 4.9 | 1.8 | 2.3 | 5.9 | 9.3 | 8.5 |
| Precision (%) | 95.1 | 98.2 | 97.7 | 94.1 | 90.7 | 91.5 |

[A]Intra- and inter-assay precision of the established in-house sandwich RNASE4 ELISA. Three different RNASE4 protein concentrations were tested in 12 rows on one plate and in 12 different plates to determine intra-assay and inter-assay variability. Coefficients of variations (CV), demonstrating variability relative to the mean, were all less than 10% and within the allowable immunoassay range.
CV: coefficient of variation.

TABLE 4

Assay validation of RNASE4 ELISA Recovery[A]

| Sample type | Average % Recovery | Range |
|---|---|---|
| Plasma[B] (n = 5) | 120 | 113-126 |

[A]Recovery was assessed by the ability to recover known amounts of recombinant RNASE4. The assay recovered average of 120% of the expected amounts of RNASE4 in plasma at working concentrations from 1 to 35 ng/ml.
[B]Plasma was diluted 1:10 prior to assay.

TABLE 5

Diagnostic accuracy of serum RNASE4 at various cut-offs

| RNASE4 cut-off (ng/ml) | Sensitivity (%) | Specificity (%) | +PV (%) | −PV (%) | +LR | −LR | Accuracy (%) |
|---|---|---|---|---|---|---|---|
| 93 | 99 | 28 | 58 | 97 | 1.4 | 0.06 | 36 |
| 109 | 95 | 69 | 76 | 94 | 3.1 | 0.06 | 82 |
| 117 | 94 | 80 | 83 | 93 | 4.7 | 0.07 | 86 |
| 131 | 80 | 93 | 92 | 81 | 12 | 0.21 | 85 |
| 141 | 62 | 97 | 95 | 72 | 19 | 0.4 | 78 |

+PV: positive predictive value, −PV: negative predictive value, +LR: positive likelihood ratio, −LR: negative likelihood ratio.

TABLE 6

Relationship between plasma PSA amount and patient demographics

PSA (ng/ml) Mean ± SEM

| Clinical features | Healthy (n = 120)[A] | P-value | Prostate Cancer (n = 120)[A] | P-value |
|---|---|---|---|---|
| Age (years) | | | | |
| 40-49 | 0.7 ± 0.1 (n = 33) | | 4.7 ± 0.7 (n = 6) | |
| 50-59 | 1.0 ± 0.1 (n = 39) | p = 0.02 | 5.9 ± 0.7 (n = 62) | p = 0.68 |
| 60-69 | 1.1 ± 0.1 (n = 32) | p = 0.01 | 5.4 ± 0.4 (n = 37) | p = 0.67 |
| 70-89 | 1.1 ± 0.2 (n = 13) | p = 0.02 | 6.7 ± 1.4 (n = 12) | p = 0.43 |
| Race/Ethnicity | | | | |
| White/Non-Hispanic | 1 ± 0.1 (n = 102) | | 5.8 ± 0.5 (n = 109) | |
| African-American | 0.8 ± 0.1 (n = 9) | p = 0.38 | 5.5 ± 0.7 (n = 6) | p = 0.86 |
| Asian | 1.8 ± 0.1 (n = 2) | p = 0.05 | 4.7 ± 0 (n = 1) | n/a |
| Caribbean/West Indian/Hispanic | 0.8 ± 0.3 (n = 2) | p = 0.61 | 3.6 ± 0 (n = 1) | n/a |
| Other | 0.8 ± 0.7 (n = 2) | p = 0.75 | n/a | n/a |

[A]Patient numbers may not add to the total sample size due to item nonresponse.

n/a = information not available.

Statistical analysis was performed by unpaired, two-tailed Student's t test.

Significant P-values >0.05 were highlighted in bold.

TABLE 7

Relationship between plasma ANG amount and patient demographics

ANG (ng/ml) Mean ± SEMI

| Clinical features | Healthy (n = 120)[A] | P-value | Prostate Cancer (n = 120)[A] | P-value |
|---|---|---|---|---|
| Age (years) | | | | |
| 40-49 | 390.2 ± 12.4 (n = 33) | | 469.3 ± 32.6 (n = 6) | |
| 50-59 | 397.4 ± 10.9 (n = 39) | p = 0.65 | 473.7 ± 12.1 (n = 62) | p = 0.91 |
| 60-69 | 356.3 ± 11.3 (n = 32) | p = 0.04 | 485.7 ± 15.8 (n = 37) | p = 0.69 |
| 70-89 | 357.0 ± 17.5 (n = 13) | p = 0.14 | 450.0 ± 25.7 (n = 12) | p = 0.66 |
| Race/Ethnicity | | | | |
| White/Non-Hispanic | 382.7 ± 7.0 (n = 102) | | 473.8 ± 9.0 (n = 109) | |
| African-American | 351.5 ± 14.9 (n = 9) | p = 0.20 | 481.6 ± 30.9 (n = 6) | p = 0.83 |
| Asian | 397.1 ± 28.6 (n = 2) | p = 0.78 | 598.7 ± 0 (n = 1) | n/a |
| Caribbean/West Indian/Hispanic | 325.5 ± 33.1 (n = 2) | p = 0.26 | 447.4 ± 0 (n = 1) | n/a |
| Other | 358.6 ± 3.7 (n = 2) | p = 0.63 | n/a | n/a |

[A]Patient numbers may not add to the total sample size due to item nonresponse.

n/a = information not avaliable.

Statistical analysis was performed by unpaired, two-tailed Student's t test.

TABLE 8

Clinical characteristics of prostate cancer patients

| Characteristic | Prostate Cancer (n = 120)[A] | RNASE4 (ng/ml) |
|---|---|---|
| Biopsy grade, n (%)[B] | | |
| 6 | 89 (74.2) | 149.0 ± 2.8 |
| 7 | 26 (21.7) | 164.1 ± 3.9 |
| 8 | 2 (1.7) | 137.4 ± 19.6 |
| 9 | 2 (1.7) | 150.6 ± 13.6 |
| Surgical Gleason, n (%)[C] | | |
| 6 | 67 (55.8) | 147.8 ± 3.1 |
| 7 | 32 (26.7) | 157.8 ± 3.3 |
| 8 | 1 (0.8) | 205.7 |
| Surgical T-stage, n (%)[D] | | |
| pT1 (1c) | 6 (5) | 129.9 ± 3.6 |
| pT2 (2a-c) | 75 (62.5) | 149.5 ± 2.7 |
| pT3 (3a-b) | 19 (15.8) | 166.8 ± 5.6 |
| Clinical T-stage, n (%)[E] | | |
| T1c | 84 (70) | 148.0 ± 2.4 |
| T2a | 17 (14.1) | 166.6 ± 6.7 |
| T2b | 8 (6.7) | 178.5 ± 4.2 |

[A]Patient numbers may not add to the total sample size due to item nonresponse.
[B]Biopsy grade score 6 (well differentiated), 7 (moderately differentiated), 8-9 (poorly differentiated)
[C]Surgical Gleason score 6 (tumor somewhat resembles normal tissue), score 7-8 (tumor resembles normal tissue barely or not at all)
[D]Surgical T-stage pathalogic pT1 (tumor identified by a needle biopsy biopsy due to an elevated serum PSA), pT2 (tumor is confined to the prostate gland), pT3 (tumor extends through the prostate capsule)
[E]Tumor stage T1c (tumor identified by a needle biopsy due to an elevated serum PSA), T2a (tumor invokes one-half of one lobe or less), T2b (tumor is in more than half of one lobe, but not both lobes)

TABLE 9

Univariate and multivariate regression analysis of RNAS4 and PSA predictive of biopsy outcome

| Outcome variable | Predictor variable | Univariate OR (95% CI) | Univariate P-value | Multivariate OR (95% CI) | Multivariate P-value |
|---|---|---|---|---|---|
| Biopsy status: Prostate cancer | PSA | 15.97 (6.44-39.60) | <0.0001 | 9.34 (3.90-22.38) | <0.0001 |
| (n = 120) vs. healthy (n = 120) | RNASE4 | 1.10 (1.08-1.13) | <0.0001 | 1.07 (1.03-1.12) | <0.0001 |
| Surgical T-stage: pT3 (n = 19) | PSA | 1.10 (0.95-1.29) | 0.19 | 1.08 (0.92-1.27) | 0.32 |
| vs. pT2 (n = 75) | RNASE4 | 1.03 (1.01-1.05) | 0.001 | 1.03 (1.01-1.06) | 0.0007 |
| Clinical stage: T2 (RNASE4, | PSA | 1.00 (0.86-1.17) | 0.97 | 0.95 (0.80-1.13) | 0.50 |
| n = 25; PSA, n = 26) vs. T1 (n = 84) | RNASE4 | 1.04 (1.02-1.06) | 0.0002 | 1.04 (1.02-1.06) | <0.0001 |
| Biopsy grade: 7 (n = 26) vs. 6 | PSA | 1.06 (0.90-1.24) | 0.47 | 1.01 (0.85-1.20) | 0.92 |
| (RNASE4, n = 89; PSA, n = 87) | RNASE4 | 1.03 (1.00-1.04) | 0.01 | 1.02 (1.00-1.04) | 0.01 |
| Surgical gleason 7 (n = 32) vs. | PSA | 1.04 (0.86-1.27) | 0.64 | 1.02 (0.84-1.26) | 0.73 |
| 6 (RNASE4, n = 84; PSA, n = 66) | RNASE4 | 1.02 (0.99-1.04) | 0.05 | 1.02 (0.99-1.04) | 0.07 |

OR: odds ratio,
CI: confidence interval
Equal n reported for PSA and RNASE4 if not stratified.
P-values ≤0.05 highlighted in bold.

TABLE 10

Histological characteristics of prostate cancer TMA cohort

| Characteristic | Prostate Cancer (n = 50)[A] |
|---|---|
| Histological grade, n (%)[B] | |
| 1-2 | 30 (60) |
| 3 | 20 (40) |
| Tumor stage, n (%)[C] | |
| T1-T2 | 27 (54) |
| T3-T4 | 23 (46) |
| Gleason score n, (%)[D] | |
| 2-3 | 27 (54) |
| 4-5 | 21 (42) |
| Distant metastasis, n (%)[E] | |
| M0 | 31 (62) |
| M1 | 15 (30) |
| Lymph node metastasis, n (%)[F] | |
| N0 | 31 (62) |
| N1-N2 | 17 (34) |

[A]Patient numbers may not add to the total sample size due to item nonresponse.
[B]Histological grade 1-2 (well-moderately differentiated), grade 3 (poorly differentiated)
[C]Tumor stage T1-T2 (tumor invades submucosa and muscularis propria), T3-T4 (tumor invades other organs or structures)
[D]Gleason scores 2-3 (predominantly well-poorly formed glands) 4-5 (only poorly formed glands or lacking gland formation)
[E]Distant metastasis M0 (no distant metastasis), M1 (distant metastasis)
[F]Lymph node metastasis N0 (no regional lymph node metastasis) N1-N2 (metastasis in 1-4 or more lymph nodes).

Other Embodiments

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features set forth herein.

All publications and patent applications mentioned in this specification are herein incorporated by reference to the same extent as if each independent publication or patent application was specifically and individually indicated as being incorporated by reference in their entirety.

It is to be understood that aspects and embodiments of the invention described herein include "comprising," "consisting," and "consisting essentially of" aspects and embodiments. Also, use of singular forms herein, such as "a" and "the," does not exclude indication of the corresponding plural form, unless the context indicates to the contrary.

Similarly, use of plural terms does not exclude indication of a corresponding singular form.

Some embodiments of the invention are within the scope of the following numbered paragraphs.

1. A method of treating or preventing prostate cancer in a subject, the method comprising administering to the subject an inhibitor of ribonuclease 4 (RNASE4).

2. The method of paragraph 1, wherein the inhibitor of RNASE4 is selected from the group consisting of a small molecule, an antibody or an antigen binding fragment thereof, an antisense RNA, or an shRNA.

3. The method of paragraph 2, wherein the antibody or an antigen binding fragment thereof is a polyclonal antibody, a monoclonal antibody, or a single chain antibody.

4. A method for identifying a subject having or at risk of prostate cancer, the method comprising determining the level of expression of RNASE4 in a sample obtained from the subject, wherein an increased level of expression of RNASE4 in the sample, as compared to a reference level, identifies the subject as having prostate cancer.

5. The method of paragraph 4, wherein the method is carried out to differentiate between benign prostate hyperplasia (BPH) and prostate cancer in the subject, and the reference level is characteristic of BPH.

6. The method of paragraph 4, wherein the method is carried out in determination of whether to carry out a needle biopsy on the subject.

7. A method for assessing the prognosis of a subject having prostate cancer, monitoring the efficacy of treatment in the subject, or selecting therapy for the subject the method comprising determining the level of expression of RNASE4 in a sample obtained from the subject, wherein an increased level of expression of RNASE4 in the sample, as compared to a reference level, indicates a subject having a poor prognosis, that the treatment is not having a beneficial effect on the subject, or that it may be beneficial to treat the subject with an inhibitor of RNASE4, respectively.

8. The method of paragraph 7, wherein the method is carried out to assess the prognosis of the subject, and the assessing of the prognosis comprises determining the risk of metastasis, level of disease aggressiveness, tumor grade, or cancer stage.

9. A method for determining the stage, sub-stage, or risk level of prostate cancer in a subject, the method comprising determining the level of expression of RNASE4 in a sample obtained from the subject with one or more reference samples.

10. The method of paragraph 9, wherein the stage, sub-stage, or risk level of prostate cancer is selected from the group consisting of: TX, T0, T1 (T1a, T1b, or T1c), T2 (T2a, T2b, or T2c), T3 (T3a, T3b, or T3c), T4, NX, N0, N1, MX, M0, M1 (M1a, M1b, or M1c), Gleason score (6 or lower, 7, 8, 9, or 10), Gleason Group (I, II, III, IV, or V), very low risk, low risk, intermediate risk, high risk, or very high risk.

11. The method of any one of paragraphs 4 to 10, wherein the sample obtained from the subject is selected from the group consisting of a sample of whole blood, serum, plasma, and prostate tissue.

12. The method of any one of paragraphs 4 to 11, further comprising determining the level of expression of prostate specific antigen (PSA) in the sample.

13. The method of any one of paragraphs 4 to 12, further comprising determining the level of expression of angiogenin (ANG) in the sample.

14. The method of any one of paragraphs 4 to 13, wherein the level of expression is determined by assessing protein expression level.

15. The method of paragraph 14, wherein the protein expression level is determined using an immunoassay.

16. The method of paragraph 15, wherein the immunoassay is an enzyme-linked immunosorbent assay (ELISA).

17. The method of paragraph 15 or 16, wherein the immunoassay employs an antibody or an antigen binding fragment thereof that is specific for RNASE4.

18. The method of paragraph 17, wherein the antibody is a monoclonal antibody, a polyclonal antibody, or a single chain antibody.

19. The method of any one of paragraphs 4 to 13, wherein the level of expression is determined by assessing mRNA expression level.

20. The method of paragraph 19, wherein the mRNA expression level is determined by qPCR, RNA-Seq, microarray analysis, gene expression profiling, or whole genome sequencing.

21. The method of any one of paragraphs 4 to 20, wherein the level of expression level of RNASE4 is increased or decreased by about 0.1, 0.25, 0.5, 1, 2, 5, or 10 fold relative to the reference level.

22. The method of any one of paragraphs 4 to 21, wherein the reference level is the expression level in a sample from the subject prior to treatment, the level in a reference population, a pre-assigned level, the level in subjects having prostate cancer, the level in subjects having prostate cancer of a particular stage, or the level in subjects having BPH.

23. The method of any one of paragraphs 4 to 22, further comprising administering a treatment for prostate cancer to the subject.

24. The method of paragraph 23, wherein the treatment for prostate cancer comprises an inhibitor of RNASE4.

25. The method of paragraph 24, wherein the inhibitor of RNASE4 is selected from the group consisting of a small molecule, an antibody or an antigen binding fragment thereof, an antisense RNA, or an shRNA.

26. The method of paragraph 25, wherein the antibody or an antigen binding fragment thereof is a polyclonal antibody, a monoclonal antibody, or a single chain antibody.

27. A method of inhibiting the growth of prostate cancer cells, the method comprising contacting the prostate cancer cells with an RNASE4 inhibitor.

28. A method of inhibiting angiogenesis in a subject having prostate cancer, the method comprising administering an RNASE4 inhibitor to the subject.

29. The method of paragraph 27 or 28, wherein the RNASE4 inhibitor is an antibody or an RNASE4 binding fragment thereof.

30. The method of paragraph 27, wherein the prostate cancer cells are present in a subject having, suspected of having, or at risk for prostate cancer.

31. A kit for identifying a subject having or being at risk for prostate cancer, the kit comprising (a) one or more polypeptides or polynucleotides that can be used to determine the level of RNASE4 protein or nucleic acid in a sample, and, optionally (b) instructions for using the one or more polypeptides or polynucleotides in an assay for the determination.

32. The kit of paragraph 31, wherein one or more polypeptides in the kit is an antibody against RNASE4 or an RNASE4 binding fragment thereof.

33. The kit of paragraph 31, wherein the one or more polynucleotides is a probe or one or more primers specific for RNASE4 nucleotide sequences.

34. The kit of any one of paragraphs 31 to 33, further comprising one or more control polypeptides or polynucleotides.

Other embodiments are within the scope of the following claims.

What is claimed is:

1. A method for identifying a subject having or at risk of prostate cancer, the method comprising determining the level of expression of RNASE4 in a blood or plasma sample obtained from the subject, wherein an increased level of expression of RNASE4 in the sample, as compared to a reference level, identifies the subject as having prostate cancer, the method further comprises treating the subject for prostate cancer, and the treatment is selected from the group consisting of prostatectomy, orchiectomy, radiotherapy, anti-androgen therapy, and provenge.

2. The method of claim 1, wherein the subject is treated by prostatectomy or orchiectomy.

3. The method of claim 1, wherein the subject is treated with brachytherapy.

4. The method of claim 1, wherein the method is carried out to differentiate between benign prostate hyperplasia (BPH) and prostate cancer in the subject, and the reference level is characteristic of BPH.

5. A method for assessing the prognosis of a subject having prostate cancer, the method comprising determining the level of expression of RNASE4 in a blood or plasma sample obtained from the subject, wherein an increased level of expression of RNASE4 in the sample, as compared to a reference level, indicates a subject having a poor prognosis, the method further comprises treating the subject for prostate cancer, and the treatment is selected from the group consisting of prostatectomy, orchiectomy, radiotherapy, anti-androgen therapy, and provenge.

6. The method of claim 5, wherein the method is carried out to assess the prognosis of the subject, the assessing of the prognosis comprises determining the risk of metastasis, level of disease aggressiveness, tumor grade, or cancer stage.

7. A method for monitoring the efficacy of treatment in a subject having prostate cancer, the method comprising determining the level of expression of RNASE4 in a blood or plasma sample obtained from the subject, wherein an increased level of expression of RNASE4 in the sample, as compared to a reference level, indicates that the treatment is not having a beneficial effect on the subject, the method further comprises treating the subject for prostate cancer, and the treatment is selected from the group consisting of prostatectomy, orchiectomy, radiotherapy, anti-androgen therapy, and provenge.

8. A method for determining the stage, sub-stage, or risk level of prostate cancer in a subject, the method comprising determining the level of expression of RNASE4 in a blood or plasma sample obtained from the subject with one or more reference samples, wherein the method further comprises treating the subject for prostate cancer, and the treatment is selected from the group consisting of prostatectomy, orchiectomy, radiotherapy, anti-androgen therapy, and provenge.

9. The method of claim 8, wherein the stage, sub-stage, or risk level of prostate cancer is selected from the group consisting of: TX, T0, T1a, T1b, T1c, T2a, T2b, T2c, T3a, T3b, T3c, T4, NX, N0, N1, MX, M0, M1a, M1b, or M1c; Gleason score of 6 or lower, 7, 8, 9, or 10; Gleason Group I, II, III, IV, or V; or very low risk, low risk, intermediate risk, high risk, or very high risk.

10. The method of claim 1, further comprising determining the level of expression of prostate specific antigen (PSA) in the sample.

11. The method of claim 1, further comprising determining the level of expression of angiogenin (ANG) in the sample.

12. The method of claim 1, wherein the level of expression is determined by assessing protein expression level.

13. The method of claim 12, wherein the protein expression level is determined using an immunoassay.

14. The method of claim 1, wherein the level of expression is determined by assessing mRNA expression level.

15. The method of claim 1, wherein the mRNA expression level is determined by qPCR, RNA-Seq, microarray analysis, gene expression profiling, or whole genome sequencing.

16. The method of claim 1, wherein the reference level is the expression level in a sample from the subject prior to treatment, the level in a reference population, a pre-assigned level, the level in subjects having prostate cancer, the level in subjects having prostate cancer of a particular stage, or the level in subjects having BPH.

17. A method of treating a subject having prostate cancer by prostatectomy, orchiectomy, radiotherapy, androgen deprivation therapy, or provenge, wherein the subject has been determined as having prostate cancer by detection of increased RNASE4 levels in a blood or plasma sample from the subject, as compared to a reference level.

18. The method of claim 17, wherein subject is treated by brachytherapy.

19. The method of claim 17, wherein the subject is treated by prostatectomy or orchiectomy.

20. The method of claim 17, wherein the anti-androgen therapy is a hormone therapy that is selected from the group consisting of luteinizing-hormone releasing (LHRH) agonist therapy, LHRH antagonist therapy or a combination thereof.

21. The method of claim 20, wherein the LHRH agonist therapy is selected from the group consisting of leuprolide, goserelin, triptorelin, and histrelin.

22. The method of claim 20, wherein the LHRH antagonist therapy is degarelix.

23. The method of claim 20, wherein the anti-androgen therapy is selected from the group consisting of bicalutamide, flutamide, nilutamide, abiraterone, and enzalutamide.

24. The method of claim 1, wherein the anti-androgen therapy is a hormone therapy that is selected from the group consisting of luteinizing-hormone releasing (LHRH) agonist, LHRH antagonist therapy, or a combination thereof.

25. The method of claim 24, wherein the LHRH agonist therapy is selected from the group consisting of leuprolide, goserelin, triptorelin, and histrelin.

26. The method of claim 24, wherein the LHRH antagonist therapy is degarelix.

27. The method of claim 24, wherein the anti-androgen therapy is selected from the group consisting of bicalutamide, flutamide, nilutamide, abiraterone, and enzalutamide.

* * * * *